(12) United States Patent
Schwartsburd et al.

(10) Patent No.: US 7,550,563 B2
(45) Date of Patent: Jun. 23, 2009

(54) METHOD FOR THE PURIFICATION OF A NON-IMMUNOGLOBULIN PROTEIN COMPRISING AN IMMUNOGLOBULIN-LIKE (IG-LIKE) DOMAIN

(75) Inventors: Boris Schwartsburd, Rehovot (IL); Ilana Belzer, Rishon-Le-Zion (IL)

(73) Assignee: Laboratoires Serono SA (CH)

( * ) Notice: Subject to any disclaimer, the term of this patent is extended or adjusted under 35 U.S.C. 154(b) by 0 days.

(21) Appl. No.: 10/567,422

(22) PCT Filed: Aug. 5, 2004

(86) PCT No.: PCT/IL2004/000732

§ 371 (c)(1), (2), (4) Date: Sep. 8, 2006

(87) PCT Pub. No.: WO2005/014621

PCT Pub. Date: Feb. 17, 2005

(65) Prior Publication Data

US 2007/0032638 A1 Feb. 8, 2007

(30) Foreign Application Priority Data

Aug. 7, 2003 (IL) ..................................... 157309

(51) Int. Cl.
*C07K 14/00* (2006.01)
*C12N 9/02* (2006.01)
(52) U.S. Cl. ................. 530/350; 530/351; 530/344; 435/189
(58) Field of Classification Search ................. 530/350, 530/351, 344; 435/189
See application file for complete search history.

(56) References Cited

FOREIGN PATENT DOCUMENTS

| EP | 0 006 035 B1 | | 7/1982 |
|---|---|---|---|
| WO | WO-99/02552 | * | 1/1999 |
| WO | WO 01/04276 A1 | | 1/2001 |
| WO | WO 03/059376 A1 | | 7/2003 |

OTHER PUBLICATIONS

Anderson, Dirk M. et al.; Nature; 390:175-179 (Nov. 13, 1997).
Bazan, J. Fernando et al.; Nature; 379:591 (Feb. 15, 1996).
Boschetti, Egisto; Trends in Biotechnology; 20(8):333-337 (Aug. 2002).
Burton, S.C. et al.; Journal of Chromatography A; 814:71-81 (1988).
Chebath, Judith et al.; European Cytokine Network; 8(4):359-365 (Dec. 1997).
Constans, Aileen; The Scientist; pp. 40-42 (Jan. 21, 2002).
Corbaz, Anne et al.; The Journal of Immunology; 168(7):3608-3616 (Apr. 1, 2002).
Engelmann, Hartmut et al.; The Journal of Biological Chemistry; 265(3):1531-1536 (Jan. 25, 1990).
Engelmann, Hartmut et al.; The Journal of Biological Chemistry; 264(20):11974-11980 (Jul. 15, 1989).
Ghayur, Tariq et al.; Nature; 386:619-623 (Apr. 10, 1997).
Halaby, D.M. et al.; Journal of Molecular Evolution; 46:389-400 (1998).
Halaby, D.M. et al.; Protein Engeering; 12(7):563-571 (1999).
Heinrich, Peter C. et al.; Biochem. J.; 334:297-314 (1998).
Jones, Simon A. et al.; The FASEB Journal; 15:43-58 (Jan. 2001).
Kim, Soo-Hyun et al.; PNAS; 97(3):1190-1195 (Feb. 1, 2000).
Kim, Soo Hyun et al.; The Journal of Immunology; 166:148-154 (2001).
Kollet, Orit et al.; Blood; 94(3);923-931 (Aug. 1, 1999).
McMahan, Catherine J. et al.; The EMBO Journal; 10(10):2821-2832 (1991).
Mühl, Heiko et al.; Biochemical and Biophysical Research Communications; 267:960-963 (2000).
Nakamura, Kyohshi et al.; Infection and Immunity; 57(2):590-595 (Feb. 1989).
Nakamura, Kyohshi et al.; Infection and Immunity; 61(1):64-70 (Jan. 1993).
Nakamura, Shuji et al.; The Journal of Immunology; 164:3330-3336 (2000).
Novick, D. et al.; FEBS; 314(3):445-448 (Dec. 1992).
Novick, Daniela et al.; Cytokine; 14(6):334-342 (Jun. 21, 2001).
Novick, Daniela et al.; J. Exp Med.; 170:1409-1414 (Oct. 1989).
Novick, Daniela et al.; Cell; 77:391-400 (May 6, 1994).
Novick, Daniela et al.; Immunity; 10:127-136 (Jan. 1999).
Okamura, Haruki et al.; Nature; 378:88-91 (Nov. 1995).
Okamura, Haruki et al.; Current Opinion in Immunology; 10:259-264 (1998).
Osborn, Laurelee et al.; The Journal of Cell Biology; 124(4):601-608 (Feb. 1994).
Pedersen, Bente Klarlund et al.; Journal of Physiology; 536.2:329-337 (2001).
Porath, Jerker et al.; Nature; 4676:1657-1659 (Jun. 13, 1959).
Puren, Adrian J. et al.; Proc. Natl. Acad. Sci. USA; 96:2256-2261 (Mar. 1999).
Schwartz, Warren et al.; Journal of Chromatography A; 908:251-263 (2001).
Simonet, W.S. et al.; Cell, 89:309-319 (Apr. 18, 1997).
Smith, Christopher; The Scientist; pp. 14-19 (Mar. 16, 1998).
Tsutsui, Hiroko et al.; The Journal of Immunology; 157:3967-3973 (1996).
Urushihara, Naoto et al.; Journal of Pediatric Surgery; 35(3):446-449 (Mar. 2000).
Ushio, Shimpei et al.; The Journal of Immunology; 156:4274-4279 (1996).
Vigers, Guy P.A. et al.; Nature; 386:190-194 (Mar. 13, 1997).
Weatherly, Gresham T. et al.; Journal of Chromatography A; 952:99-100 (2002).
Xiang, Yan et al.; Virology; 257:297-302 (1999).
Yasuda, Histaka et al.; Endocrinology; 139:1329-1337 (1998).

\* cited by examiner

*Primary Examiner*—Chih-Min Kam
(74) *Attorney, Agent, or Firm*—Nixon Peabody LLP

(57) ABSTRACT

The present invention relates to a method for the purification of non-immunoglobulin proteins comprising one or more immunoglobulin-like (Ig-like) domain.

18 Claims, 7 Drawing Sheets

METHOD FOR THE PURIFICATION OF A NON-IMMUNOGLOBULIN PROTEIN COMPRISING AN IMMUNOGLOBULIN-LIKE (IG-LIKE) DOMAIN

CROSS-REFERENCE TO RELATED APPLICATIONS

This application is a 371 National Phase Entry Application of co-pending International Application PCT/IL2004/000732, filed Aug. 5, 2004, which designated the U.S. and which claims the benefit under 35 U.S.C. § 119 of Application No. IL 157309, filed Aug. 7, 2003.

FIELD OF THE INVENTION

The present invention relates to a method for the purification of non-immunoglobulin proteins comprising one or more immunoglobulin-like (Ig-like) domain.

BACKGROUND OF THE INVENTION

A large number of human and other mammalian proteins, including, for example, human growth hormone, human protein C clotting Factor VII and IL-18BP have been produced in host cells by transfecting these cells with DNA encoding these proteins and growing the recombinant cells under conditions favourable for the expression of the protein. Recombinant proteins can be produced also by transgenic animals and secreted into the milk. The recombinant proteins are secreted by the cells into the cell culture medium, into the milk or are present in cell lysates and must be separated from other cell components, such as cell waste products, cell debris and proteins or other collected material. Protein purification usually requires some type of chromatography separation (see review by Constans 2002).

The following chromatographic separations are widely used: gel filtration (GF), ion exchange (IEX), hydrophobic interaction (HI) chromatography, affinity chromatography and HPLC (high-performance liquid chromatography).

Protein purification generally takes place in three phases: a capture step, in which the desired protein is separated from other cellular components such as DNA and RNA; an intermediate step, in which proteins are isolated from contaminants similar in size or other physical/chemical properties; and finally a polishing step. Each purification stage have certain chromatography techniques and bead sizes that are best suited to the specific protein being purified.

The initial capture step typically involves protein isolation from a crude cell lysate or from cell culture medium and requires a resin with a high capacity and high flow rate. "Fast flow" resins with a large bead size and large bead size range (the range can vary widely from the average bead size) are suitable for this purpose.

Immunoglobulin (Ig) is defined as any of the structural cell antigen receptors; it is divided into five classes (IgM, IgG, IgA, IgD and IgE) on the basis of structure and biologic activity. The basic structural unit of the immunoglobulin molecule, referred to as a monomer, is a Y-shaped molecule composed of two heavy (H) chains having four domains each: one variable $V_H$ and three constant $C_H$ domains) and two light (L) chains having two domains each: one variable $V_L$ and one constant $C_L$ domain. $V_H$ and $V_L$ make up the antigen-binding site. The basic pattern of the immunoglobulin domains consists of two antiparallel, twisted β-sheets that surround an internal volume tightly packed with hydrophobic side chains (i.e. hydrophobic core). Depending on the degree of curvature of the sheets, the overall shape of the domain can be described either as a cylinder (β-barrel) or, if the two layers are straight, as a sandwich-like structure. The two β-sheets are covalently linked by a strongly but not rigorously conserved intra-chain disulfide bridge (Encyclopedia of Immunology Eds Roitt and Delves 1992, p92-93 and p476-477).

Ig-like domains have been identified in proteins from various kingdoms including eukaryotes and prokaryotes, including virus fungi and plants (Halaby et al. 1998). Ig-like domains are found in many proteins for example, in the bacterial enzymes β-galactosidase and chitinase A, in human receptors such as the growth hormone receptor, in cytokine receptors such as the IL-1 receptor (McMahan et al 1991), IL-6 receptor (Vollmer et al 1999) and human tissue factor (HFT) receptor (Halaby et al. 1999), in thyrosine kinase receptors that transduce growth factor dependent signals to the intracellular environment (Wiesmann et al. 2000), in immunoglobulin related proteins such as CD4, and in extracellular matrix proteins such as Fibronectin type III (Halaby et al. 1999).

Typically, Ig-like domains are composed of 7-10 β-strands, distributed between two sheets with specific topology and connectivity. Fifty-two 3D structures of Ig-like domains covering the immunoglobulin fold family (IgFF) were compared (Halaby et al. 1999) and the results show that most of the Ig-like domains display less than 10% sequence identity and that in the Ig-like domains most of the residues constituting the common core are hydrophobic. Thus, Ig-like domains have more structural than sequence similarities. The hydrophobic core has a major impact on the uniqueness and stability of the Ig fold. Despite the wide sequence variations in Ig-like domains, the maintenance of the Ig-fold seems to be enhanced by a conserved geometry of hydrogen bonds. Some proteins have more than one Ig-like domain, for example the mature type II IL-1 receptor has three immunoglobulin-like domains (McMahan et al. 1991) and the adhesion molecule VCAM has 7 Ig-like domains (Osborn et al. 1994).

The following are examples of important proteins having Ig-like domains: adhesion molecules such as NCAM (5 Ig-like domains), Fibronectin type III, ICAM-1, mad CAM-1, PECAM-1, VCAM-1, titin and cadherin, neurocan, extracellular domains of cytokine receptors such as LIFR, CNTFR, IL-3R, IL5R, IL-6R, IL-12R, GM-CSFR and OSMR, growth factor receptors such as Vascular endothelial growth factor (VEGF) receptor (7 Ig-like domains), fibroblast growth factor (FGF) receptor, human platlet-derived growth factor (hP-DGF) receptor, immune related receptors such as T cell receptor, major histocompatibility complex (MHC) proteins, macrophage colony stimulatory factor 1 receptor (CSF-1R), microglobulin-β, CTLA4 a receptor in T cells for B7 molecules (two Ig-like domains), B7 a B cell activation agent which regulates T cell proliferation and others such as neuregulin, coagulation factor XIII, NF-kB, superoxide dismutase and IL-18 binding protein.

Cytokine binding proteins usually consist of the extracellular ligand binding domains of their respective cell surface cytokine receptors (soluble cytokine receptors). The soluble receptors are produced either by alternative splicing or by proteolytic cleavage of the cell surface receptor. These soluble receptors have been described in the past: for example, the soluble receptors for IL-6 and IFN-γ (Novick et al. 1989), TNF (Engelmann et al. 1989 and Engelmann et al. 1990), IL-1 and IL-4 (Maliszewski et al. 1990) and IFN-α/β (Novick et al. 1994, Novick et al. 1992). One cytokine-binding protein, named osteoprotegerin (OPG, also known as osteoclast inhibitory factor—OCIF), a member of the TNFR/Fas family, appears to be the first example of a soluble receptor that exists only as a secreted protein (Anderson et al. 1997, Simonet et al. 1997, Yasuda et al. 1998).

An interleukin-18 binding protein (IL-18BP) which abolishes IL-18 induction of IFN-γ and IL-18 activation of NF-kB in vitro is known (Novick et al. 1999). IL-18BP is a soluble receptor that exist only as a secreted protein. IL-18BP has a single Ig-like domain and resembles the extracellular segment of cytokine receptors comprising Ig-like domains.

Another non-immunoglobulin protein comprising an Ig-like domain is the receptor for interleukin-6 (IL-6R). In the literature interleukin-6 has been proposed to act both as pro- and anti-inflammatory cytokine (reviewed in Heinrich et al., 1998, Jones et al. 2001 and Pedersen et al. 2001). The receptor complex mediating the biological activities of IL-6 consist of two distinct membrane bound glycoproteins, an 80 kDa cognate receptor subunit (IL-6R) and a 130 kDa signal-transducing element (gp130, CD130). Expression of gp130 is ubiquitous, in contrast, cellular distribution of IL-6R is limited and is predominantly confined to hepatocytes and leukocyte subpopulations. In addition to the membrane bound receptor, a soluble form of the IL-6R (sIL-6R) has been purified from human serum and urine. This soluble receptor binds IL-6 and prolongs its plasma half-life. More importantly the sIL-6R/IL-6 complex is capable of activating cells via interaction with gp130. This feature makes the sIL-6R/IL-6 complex an agonist for cell types that although they express gp130, would not inherently respond to IL-6 alone. Hence, the sIL-6R has the ability to widen the repertoire of cell types that are responsible to IL-6.

By fusing the entire coding regions of the cDNAs encoding the soluble IL-6 receptor (sIL-6R) and IL-6, a recombinant IL6-IL6R chimera was produced in human cells (Chebath et al. 1997). This IL6-IL6R chimera has enhanced IL-6-type biological activities and it binds with a much higher efficiency to the gp130 chain in vitro than does the mixture of IL-6 with sIL-6R (Kollet et al. 1999).

Mercapto-ethyl-pyridine (MEP) HYPERCEL® (Bio-Sepra) is a Hydrophobic Charge Induction Chromatography (HCIC) resin. This resin was specifically designed to capture immunoglobulins (Boschetti 2000 and Life technologies Inc. 2000). At neutral pH, hydrophobic capture occurs in HCIC resin by both an aliphatic-hydrophobic spacer and a neutral (uncharged) pyridine ring. In contrast to HI chromatography, adsorption of antibodies from cell culture supernatants on HCIC resin is accomplished without the need of any pH or ionic strength adjustment. Once the pH is lowered from pH 7.2 to pH 4, the pyridine ring in the resin and the bound antibody become positively charged, due to charge repulsion, the immunoglobulins detaches and elutes from the column. Although this chromatography method is used for the capture of immunoglobulin, it could not be predicted that it would work for the capture of non-immunoglobulin proteins having an IgG-like domain, since the immunoglobulins have a distinctive sequences and moreover since the IgG-like domain in 52 different non-immunoglobulin proteins has less than 10% sequence identity (Halaby et al. 1999).

The present invention relates to a method for purifying non-immunoglobulin proteins having Ig-like domains from a biological fluid.

SUMMARY OF THE INVENTION

The invention relates to a method for purifying or capturing a non-immunoglobulin protein of interest having between one and ten immunoglobulin-like (Ig-like) domains from a biological fluid, comprising the steps of:

a) contacting the biological fluid containing the protein of interest with an Hydrophobic Charge Chromatography (HCIC) resin,
b) washing out the resin to remove unbound contaminants,
c) eluting the protein of interest by treating the resin with a solution having an acidic pH or with a solution comprising an organic solvent.

In one embodiment of the method of the invention, the HCIC resin is MEP-HYPERCEL®.

In another embodiment of the method of the invention, the organic solvent used in step c) is propylene glycol, preferable in a solution containing propylene glycol at a concentration between about 25 and 50%.

In a further embodiment of the invention, step a) is carried out at acidic pH, preferably at a pH between about 3 and 6.8.

In a second further embodiment of the invention, step b) is carried out with a solution having an acidic pH, preferably between about 3 and 6.8.

In one aspect of the invention, the protein of interest is in a biological fluid selected from a cell-conditioned culture medium, cell lysate, cell extract, tissue extract, blood plasma, serum, milk, urine, ascites, cerebrospinal fluid, vegetable juice, plant extracts or a fraction derived from an earlier chromatographic separation step.

In a further embodiment of the invention, the protein of interest has 1 to 7 Ig-like domains.

The invention provides a method for the purification or capturing a protein of interest such as I NCAM, Fibronectin type III, ICAM-1, mad CAM-1, PE CAM-1, VCAM-1, titin, cadherin, neurocan, LIFR, CNTFR, IL-1R, IL-3R, IL5R, IL-6R, IL-12R, GM-CSFR, OSMR, VEGF receptor, FGF receptor, hPDGF receptor, T cell receptor, MHC proteins, microglobulin-β, CTLA4, B7 activation agent, neuregulin, coagulation factor XIII, NF-kB, IL6-IL6R, superoxide dismutase and preferably IL-18BP, IL6-IL6R chimera or beta galactosidase or an isoform, mutein, fused protein, functional derivative or fragment thereof comprising at least one Ig-like domain.

In one embodiment, the method of the invention allows obtaining a purified protein with a purification factor in the range of II and 94 fold, preferably about 94 fold.

In a further embodiment, the invention allows obtaining a purified protein with a concentration factor in the range of 1.5 and 3.1 fold, preferably 3.1 fold.

Also, the method of the invention allows obtaining a purified protein with a yield in the range of 73 and 98%, preferably about 85%. In addition, the invention provides for the use of a hydrophobic charge chromatography (HCIC) resin for capturing a non-immunoglobulin protein of interest having between one and ten immunoglobulin-like (Ig-like) domains from a biological fluid, comprising the steps of:

a) contacting the biological fluid containing the protein of interest with an HCIC resin,
b) washing out the resin to remove unbound contaminants,
c) eluting the protein of interest by treating the resin with a solution having an acidic pH or with a solution comprising an organic solvent.

In one aspect, the invention provides a purified protein preparation comprising a non-immunoglobulin protein of interest having between 1 and 10 immunoglobulin-like (Ig-like) domains, purified or captured from a biological fluid by the method of the invention.

In a further embodiment of the invention, the purified protein preparation is selected from IL-18BP, NCAM, Fibronectin type III, ICAM-1, mad CAM-1, PE CAM-1, VCAM-1, titin, cadherin, neurocan, LIFR, CNTFR, IL-1R, IL-3R, IL5R, IL-6R, IL-12R, GM-CSFR, OSMR, VEGF receptor, FGF receptor, hPDGF receptor, T cell receptor, MHC proteins, microglobulin-β, CTLA4, B7 activation agent, neuregulin, coagulation factor XIII, NF-kB, IL6-IL6R, beta-galactosidase and superoxide dismutase, preferably IL-18BP, IL6-IL6R and beta galactosidase or an isoform, mutein, fused protein, functional derivative or fragment thereof, comprising at least one Ig-like domain.

DETAILED DESCRIPTION OF THE INVENTION

Figure 1:
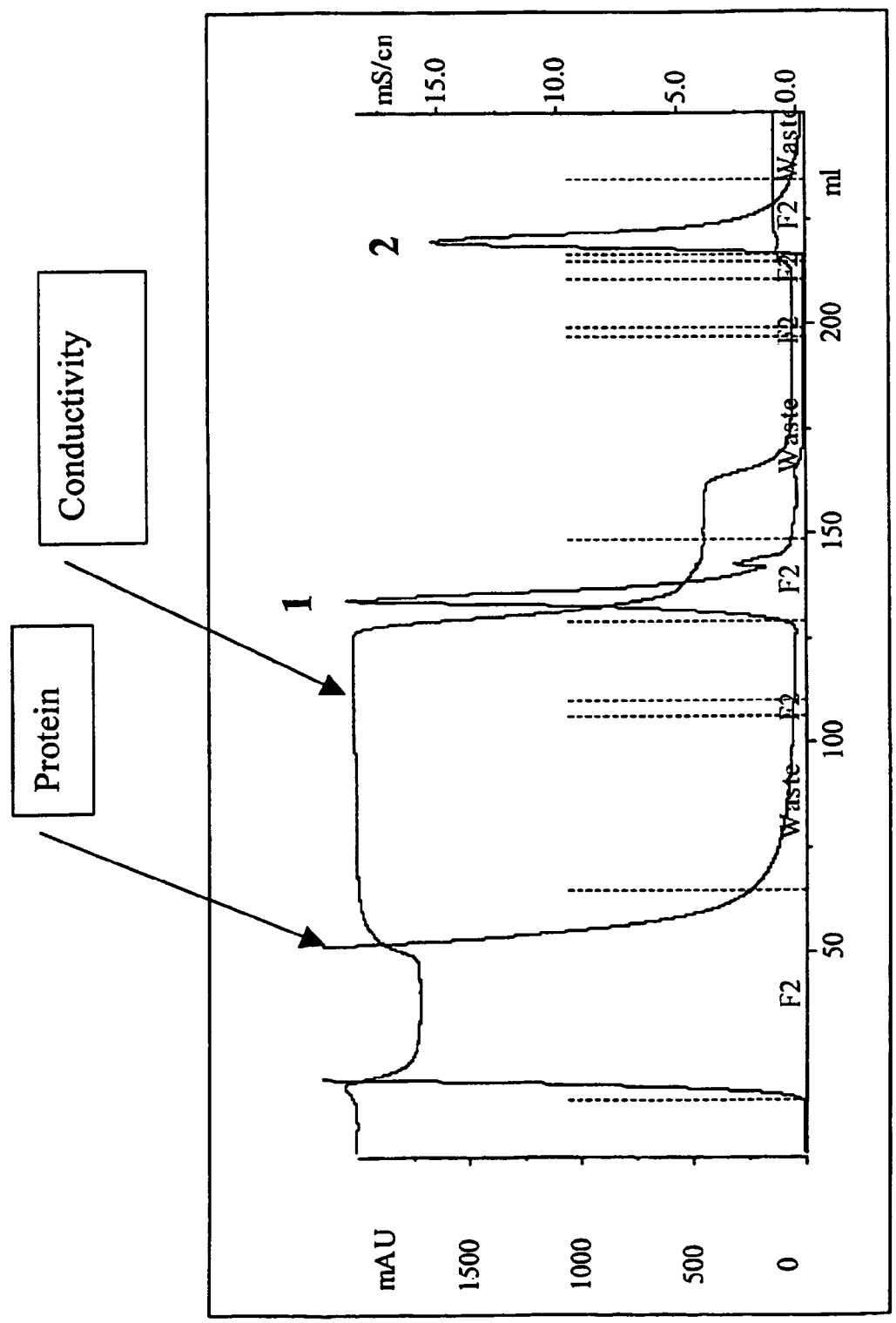
FIG. 1 shows a chromatogram obtained in the capture of IL-18BP in a two-step (35%-50%) propylene glycol (PG) elution on a MEP-HYPERCEL® column.
Run Data:
Column bed volume: 5 ml.
Equilibration buffer: PBS (buffered phosphate saline), 10 mM sodium phosphate, 150 mM sodium chloride, pH 7.2 prepared by 1:10 dilution of 10×PBS, IPL Code No. S88RD005.)-flow rate 3 ml/min.
Load: concentrated crude material (CCM) containing 0.50 mg/ml r-hIL-18BP (ELISA) and 32 mg/ml total protein (Bradford)—flow rate 1 ml/min.
Washes: 1) PBS pH 7.2, 2) 50 mM acetate pH 4.5 (peak 1), 3) water for injection (WFI)-flow rates of all washes 3 ml/min.
First elution: 35% propylene glycol in 20 mM phosphate buffer at pH 8.4 (peak 2)—flow rate 1 ml/min.
Second elution: in 50% PG. The left ordinate indicates absorption at A280 (protein mAU units), the right ordinate indicates conductivity (mS/crr units) in the abscissa is denoted the volume flowing through the column (ml).

The present invention is based on the finding that non-immunoglobulin proteins comprising one or more Ig-like domain are efficiently captured from biological fluids by MEP HYPERCEL® resin, a resin which is typically used for the capture of immunoglobulins.

Thus, invention relates to a method for purifying and or capturing a non-immunoglobulin protein of interest having between 1 and 10 immunoglobulin-like (Ig-like) domains from a biological fluid comprising the steps of:
a) contacting the biological fluid containing the protein of interest with an Hydrophobic Charge Chromatography (HCIC) resin,
b) washing out the resin to remove unbound contaminants,
c) eluting the protein of interest by treating the resin with a solution having an acidic pH or with a solution comprising an organic solvent.

Mercapto-ethyl-pyridine (MEP) HYPERCEL® (Bio-Sepra) is a Hydrophobic Charge Induction Chromatography (HCIC) resin. This resin was specifically designed to capture immunoglobulins (Boschetti 2000 and Life technologies Inc. 2000). At neutral pH, hydrophobic capture occurs in HCIC resin by both an aliphatic-hydrophobic spacer and a neutral (uncharged) pyridine ring. In contrast to HI chromatography, adsorption of antibodies from cell culture supernatants on HCIC resin is accomplished without the need of any pH or ionic strength adjustment. Once the pH is lowered from pH 7.2 to pH 4, the pyridine ring in the resin and the bound antibody become positively charged, due to charge repulsion, the immunoglobulins detaches and elutes from the column. Although this chromatography method is used for the capture of immunoglobulin, it could not be predicted that it would work for the capture of non-immunoglobulin proteins having an IgG-like domain, since the immunoglobulins have a distinctive sequences and moreover since the IgG-like domain in 52 different non-immunoglobulin proteins has less than 10% sequence identity (Halaby et al. 1999).

In one embodiment of the invention, the possibility of capturing a non-immunoglobulin protein comprising an Ig-like domain with the HCIC resin, MEP HYPERCEL®, was exemplified with IL-18BP. IL-18BP is highly glycosylated and consequently is more acidic (isoelectric point of about 3) and less hydrophobic than immunoglobulins. On the one hand, binding of immunoglobulins to MEP HYPERCEL® is based on hydrophobicity, and contrary to immunoglobulins, IL-18BP is not very hydrophobic. On the other hand, even if IL-18BP binds to such resin, the conditions recommended to elute antibodies were not expected to work for IL-18BP, since changing the pH from pH7.2 to pH4 does not cause IL-18BP to became positively charged and therefore IL-IBP under such pH conditions is expected to remain bound to the column. Thus, the use of MEP HYPERCEL® resin for the capture of IL-18BP would be considered inadequate by the skilled in the art due to the physico-chemical characteristics of the protein and the binding and elution principles of the resin.

In one embodiment, concentrate crude material (CMM) (Example 1, FIG. 1) containing IL-18BP was applied into a MEP HYPERCEL® pre-equilibrated column (buffer (PBS) at pH 7.2). The column was washed with the same buffer to remove unbound proteins. Taking advantage of the differential physico-chemical properties of immunoglobulines (isoelectric point in the range of 6-6.5) and IL-18BP (isoelectric point of about 3), and according to the manufacturer instructions for immunoglobulin purification, immunoglobulin contaminants were washed away from the column by decreasing the pH to 4.5, at which pH IL-18BP remains bound to the resin. Finally, in order to recover the IL-18BP from the column, a solution containing propylene glycol (about 35% propylene gycol in phosphate buffer) at pH 8.4 was successfully employed.

The results obtained show that IL-18BP efficiently binds to the MEP HYPERCEL® resin and that the protein is eluted from the resin as a discrete peak.

It was shown that the capture of non-immunoglobulin proteins comprising an Ig-like domain on the MEP HYPERCEL® column can be optimised, as demonstrated in the examples below, by varying chromatographic parameters such as flow rates, buffer compositions, pH of loading material, column capacity etc. For example, the characteristic that the immunoglobulin fraction is eluted from the MEP HYPERCEL® column at acidic pH (pH 4, Boschetti 2000 and Life technologies Inc. 2000) was exploited in order to increase the loading column capacity of IL-18BP. The pH of the loading material can be adjusted to a more acidic pH (such as pH 6.1) to adsorb less immunoglobulins and more r-hIL-18BP on the column during the loading step and remove as much as possible of the contaminating immunoglobulins. In the examples below it is demonstrated that by loading the crude material at lower pH, an increase in IL-18BP capacity of about two-fold and higher was obtained.

As demonstrated by SDS-PAGE (Example 5) analysis, RP-HPLC (Example 7) and enzyme linked immuno sorbant assay (ELISA) (Example 6), the MEP HYPERCEL® column capture step has a good loading capacity (about 6 mg IL-18BP/ml resin), high recovery (≧85%) and purification efficacy for IL-18BP. Also, the purified r-hIL-18BP fraction elutes in a narrow peak. The high performance of the MEP HYPERCEL® resin in the capture of IL-18BP is most likely due to the selective binding of r-hIL-18BP to the resin, the efficient wash step in acidic pH and the elution conditions selected (elution with PG).

In addition, using various MEP HYPERCEL® resin batches in the capture of r-hIL-18BP it was demonstrated batch to batch results consistency.

Additional experiments show that the performance of the MEP HYPERCEL® column is similar using material produced in serum free medium or in medium supplemented with serum.

Therefore the presence or absence of serum in the starting material or crude harvest does not affect the binding the protein to a MEP HYPERCEL® column.

In another embodiment of the invention, the possibility of capturing a non-immunoglobulin protein comprising an Ig-like domain with the MEP HYPERCEL® resin was exemplified with r-hIL6-IL6R chimera produced by CHO cells. hIL6-IL6R chimera (also called "IL6R/IL6" or "IL-6 chimera"), is a chimeric molecule comprising a soluble part of the interleukin-6 receptor (sIL-6R), bearing an Ig-like domain, fused to interleukin-6.

The material applied to the column was crude harvest produced by recombinant CHO cells comprising 2% FBS, which was obtained after clarification and 20 fold concentration (Example 8).

More specifically, the crude harvest of r-hIL6-IL6R chimera produced in CHO cells was loaded onto a MEP HYPERCEL® column equilibrated with PBS. After washing the column, the captured material was eluted with 35% PG. The amount of protein in the eluted fraction was analyzed by ELISA and by SDS-PAGE. The results show that the MEP HYPERCEL® column has a capacity of above 2 mg r-hIL6-IL6R per ml resin, a yield of about 72%, and purification factor of about 94 fold for the capture of r-hIL6-IL6R.

It is shown by SDS-PAGE (FIG. 5) that the r-hIL6-IL6R chimera, which was essentially undetectable in the crude harvest, appears as one of the major bands in the MEP HYPERCEL® eluted fraction (94 fold purification by ELISA).

In order to check the contribution of the Ig-like domain within the r-hIL6-IL6R chimera to the binding to the MEP HYPERCEL® column, binding of IL-6 alone to the Mep HYPERCEL® column was explored. For this purpose, the crude harvest of CHO recombinant cells was applied to the column of MEP HYPERCEL® using similar conditions as those employed for the intact chimera. It was found that IL-6 alone, in contrast to the IL6-IL6R chimera containing the Ig-like domain, does not bind to the column.

The use of MEP HYPERCEL® resin for the capture of non-immunoglobulin Ig-like comprising proteins was exemplified in a further embodiment with the bacterial enzyme, r-beta-galactosidase. This enzyme contains an Ig-like domain type C3 (Halaby et al. 1999). r-beta-galactosidase was spiked in serum free medium (Example 9) and applied to the MEP HYPERCEL® column. After wash of the column, the captured material was eluted with 35% PG. Fractions corresponding to unbound and eluted material were collected and analysed by SDS-PAGE. The results obtained show that the MEP HYPERCEL® resin, efficiently captures the beta-galactosidase enzyme from the solution.

The above examples demonstrate that the HYPERCEL® resin can be used for purification of different non-immunoglobulin proteins comprising an Ig-like domain.

The invention relates to the capture of non-immunoglobulin proteins comprising one or more Ig-like domain/s by Mep HYPERCEL®, or by HCIC resins comprising the same or similar characteristics to Mep HYPERCEL®, which allows capture of proteins comprising one or more Ig-like domains. The invention relates also to the capture of a non-immunoglobulin protein which do not naturally have Ig-like domains, but to which such a domain has been fused by recombinant methods.

Ig-like domain containing proteins can be captured from a biological fluid or cell lysate using a HCIC resin such as MEP HYPERCEL®. The capture in a general sense involves contacting the biological fluid or cell extract with the Ig-like domain containing protein of interest with the HCIC resin such MEP HYPERCEL®, washing out the resin to remove unbound contaminants and eluting the bound material by changing the environment pH, or as described in a specific embodiment by applying an organic solvent such as isopropyl alcohol or propylene glycol and/or polyalcohols for example glycerol, polyethylene glycol (e.g. between about 25-50%).

Contacting the biological fluid or cell extract with the HCIC, could be carried out at the pH of the crude harvest or neutral PH or alternatively prior to contacting, the pH of the column and the crude harvest could be adjusted to acidic pH e.g. pH between 3-6.8, like for the purification of IL-18BP or to basic pH.

For washing out the resin to remove unbound contaminants, solutions which have the same PH as the loaded material (for example PBS 7.2) and/or neutral PH can be used, and/or a solution with acidic (e.g. pH 3-6.8) or basic PH could be used. Recombinant proteins comprising Ig-like domains can be produced either in bacterial or eukaryotic (e.g. CHO) cultured host cells transfected with vectors encoding such proteins or in transgenic animals or plants. When using transgenic animals it is particularly advantageous to produce heterologous proteins in their milk. Dairy animals such as cattle, sheep and goats are thus preferred hosts. See, for example, WIPO Publications WO 88/00239, WO 90/05188, WO 91/02318, and WO 92/11757; and U.S. Pat. Nos. 4,873,191; 4,873,316; and 5,304,489, which are incorporated herein by reference in their entirety.

Thus, non-immunoglobulin proteins comprising Ig-like domains including isoforms, muteins, fused proteins, functional derivatives or fragment thereof, provided that they have preserved at least one Ig-like domain, can be captured using the method of the invention from the medium of recombinant cells, cell lysates, from milk of the transgenic animals, transgenic plants, urine, ascites, vegetable juice, plant extracts etc.

Thus using the method of purification of non-immunoglobulin proteins of interest according to the invention it is possible to obtain a purified protein preparation of NCAM (5 Ig-like domains), fibronectin type III, ICAM-1, mad CAM-1, PE CAM-1, VCAM-1, titin and cadherin, neurocan, extracellular domains of cytokyne receptors such as LIFR, CNTFR, IL-3R, IL5R, IL-6R, IL6-IL6R, IL-12R, GM-CSFR and OSMR, growth factor receptors such as vascular endothelial growth factor (VEGF) receptor (7 Ig-like domains), fibroblast growth factor (FGF) receptor, human platlet-derived growth factor (hPDGF) receptor, immune related receptors such as T cell receptor, major histocompatibility complex (MHC) proteins, microglobulin-β, CTLA4 a receptor in T cells for B7 molecules (two Ig-like domains), B7 a B cell activation agent which regulates T cell proliferation and others such as neuregulin, coagulation factor XIII, NF-kB, superoxide dismutase and IL-18BP (one Ig-like domain).

Preferably, in the method of capture and or purification of a non-immunoglobulin protein having one or more Ig-like domains, according to the invention, the purification factor of the protein obtained is in the range of 11-94 fold and more preferably about 94 fold, the concentration factor of the protein obtained is in the range of 1.5-3.1 fold, more preferably about 5 fold and the yield of the protein obtained is in the range of 73 and 85%, more preferably about 98%.

Typically, immunoglobulin-like (Ig-like domains are composed of 7-10 β-strands, distributed between two sheets with specific topology and connectivity. Fifty-two 3D structures of Ig-like domains covering the immunoglobulin fold family (IgFF) were compared (Halaby et al. 1999) and the results show that most of the Ig-like domains display less than 10% sequence identity and that in the Ig-like domains most of the residues constituting the common core are hydrophobic. Thus, Ig-like domains have more structural than sequence similarities. The hydrophobic core has a major impact on the uniqueness and stability of the Ig fold. Despite the wide sequence variations in Ig-like domains, the maintenance of the Ig-fold seems to be enhanced by a conserved geometry of hydrogen bonds. Some proteins have more than one Ig-like domain, for example the mature type II IL-1 receptor has three immunoglobulin-like domains (McMahan et al. 1991) and the adhesion molecule VCAM has 7 Ig-like domains (Osborn et al. 1994).

The following are examples of important proteins having Ig-like domains: adhesion molecules such as NCAM (5 Ig-like domains), Fibronectin type III, ICAM-1, mad CAM-1, PE CAM-1, VCAM-1, titin and cadherin, neurocan, extracellular domains of cytokine receptors such as LIFR, CNTFR, IL-3R, IL5R, IL-6R, IL-12R, GM-CSFR and OSMR, growth factor receptors such as Vascular endothelial growth factor (VEGF) receptor (7 Ig-like domains), fibroblast growth factor (FGF) receptor, human platlet-derived growth factor (hPDGF) receptor, immune related receptors such as T cell receptor, major histocompatibility complex (MHC) proteins, macrophage colony stimulatory factor 1 receptor (CSF-1R), microglobulin-β, CTLA4 a receptor in T cells for B7 molecules (two Ig-like domains), B7 a B cell activation agent which regulates T cell proliferation and others such as neuregulin, coagulation factor XIII, NF-kB, superoxide dismutase and IL-18 binding protein.

As used herein the term "muteins" refers to analogs of a non-immunoglobulin protein comprising an Ig-like domain, in which one or more of the amino acid residues of the protein, e.g. IL-18BP, IL6-IL6R, IL-6R and beta-galactosidase are replaced by different amino acid residues, or are deleted, or one or more amino acid residues are added to them, without changing considerably the activity of the resulting products as compared with IL-18BP, IL6-IL6R, IL-6R and beta-galactosidase and/or provided that they have preserved at least one Ig-like domain. More specifically, one or more amino acids of the proteins, but no more than 30, preferably no more than 20, more preferably no more than 10, most preferably one or two amino acids, may be replaced with other amino acids, or eliminated, or may be added. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes a non-immunoglobulin protein comprising at least 1 Ig-like domain such as e.g. IL-18BP, IL6-IL6R, IL-6R and beta-galactosidase, in accordance with the present invention, under stringent conditions. The term "stringent conditions" refers to hybridisation and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al., supra. Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of a non-immunoglobulin protein comprising at least an Ig-like domain such as IL-18BP, IL6-IL6R, IL-6R and beta-galactosidase, such as to have substantially similar activity to IL-18BP, IL6-IL6R, IL-6R and beta-galactosidase and/or provided that they have preserved at least one Ig-like domain.

In a preferred embodiment, any such mutein has at least 40% identity or homology with the amino acid sequence of e.g. IL-18BP, IL6-IL6R, IL-6R and beta-galactosidase. More preferably, it has at least 50%, at least 60%, at least 70%, at least 80% or, most preferably, at least 90% identity or homology thereto.

Muteins, which can be purified in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of non-immunoglobulin protein comprising at least an Ig-like domain such as IL-18BP, IL6-IL6R, IL-6R and beta-galactosidase, may include synonymous amino acids within a group which have sufficiently similar physicochemical properties that substitution between members of the group will preserve the biological function of the molecule (Grantham, 1974) and/or provided that they have preserved at least one Ig-like domain. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues and/or provided that they have preserved at least one Ig-like domain. Proteins and muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |

TABLE A-continued

Preferred Groups of Synonymous Amino Acids

| Amino Acid | Synonymous Group |
|---|---|
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE C

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in non-immunoglobulin protein comprising an Ig-like domain which can be used for obtaining muteins of e.g. IL-18BP, IL6-IL6R, IL-6R and beta-galactosidase proteins, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a non-immunoglobulin protein comprising an Ig-like domain, e.g. IL-18BP, IL6-IL6R, IL-6R and beta-galactosidase or a mutein or fragment thereof, fused with another non-immunoglobulin protein, which, e.g., has an extended residence time in body fluids. E.g. IL-18BP, IL6-IL6R, IL-6R and beta-galactosidase may thus be fused to another non-immunoglobulin protein, polypeptide or the like.

"Functional derivatives" as used herein cover derivatives of proteins containing an Ig-like domain, e.g. IL-18BP, IL6-IL6R, IL-6R and beta-galactosidase and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of e.g. IL-18BP, IL6-IL6R, IL-6R and beta-galactosidase and/or provided that they have preserved at least one Ig-like domain.

These derivatives may, for example, include polyethylene glycol side☐chains, which may mask antigenic sites and extend the residence of a protein in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "fragments" of a protein comprising an Ig-like domain and or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to the protein such as IL-18BP, IL6-IL6R, IL-6R and beta-galactosidase and/or provided that they have preserved at least one Ig-like domain.

The invention refers also to proteins comprising an Ig-like domain such as IL-18BP, IL6-IL6R, IL-6R and beta-galactosidase or an isoform, a mutein, fused protein, functional derivative, active fraction or circularly permutated derivative thereof, provided that they have preserved at least one Ig-like domain.

The following are examples of some important proteins comprising Ig-like domains: adhesion molecules such as NCAM (5 Ig-like domains), fibronectin type III, ICAM-1, mad CAM-1, PE CAM-1, VCAM-1, titin and cadherin, neurocan, extracellular domains of cytokyne receptors such as LIFR, CNTFR, IL-3R, IL5R, IL-6R, IL6-IL6R, IL-12R, GM-CSFR and OSMR, growth factor receptors such as vascular endothelial growth factor (VEGF) receptor (7 Ig-like domains), fibroblast growth factor (FGF) receptor, human platlet-derived growth factor (hPDGF) receptor, immune related receptors such as T cell receptor, major histocompatibility complex (MHC) proteins, microglobulin-β, CTLA4 a receptor in T cells for B7 molecules (two Ig-like domains), B7 a B cell activation agent which regulates T cell proliferation and others such as neuregulin, coagulation factor XIII, NF-kB, superoxide dismutase and IL-18BP (one Ig-like domain).

The term "IL-18 binding proteins" is used herein synonymously with "IL18-BP". It comprises IL-18 binding proteins as defined in WO 99/09063 or in Novick et al., 1999, including splice variants and/or isoforms of IL-18 binding proteins, as defined in Kim et al., 2000. In particular, human isoforms a and c of IL-18BP are useful in accordance with the presence invention. The proteins useful according to the present invention may be glycosylated or non-glycosylated, they may be derived from natural sources, such as urine, or they may preferably be produced recombinantly. Recombinant expression may be carried out in prokaryotic expression systems like $E.\ coli$, or in eukaryotic, and preferably in mammalian, expression systems.

"Biological fluid" denotes any fluid derived from or containing cells, cell components or cell products. Biological fluids include, but are not limited to, cell culture supernatants, cell lysates, cleared cell lysates, cell extracts, tissue extracts, blood, plasma, serum, milk urine, ascites, vegetable juice, plant extracts and fractions thereof and also a fraction derived from another chromatographic separation step. The biological fluid to be used as crude material, in the capture step of non-immunoglobulin proteins comprising at least one Ig-like domain, according to the invention can be concentrated, non-concentrated or diluted.

Cell culture supernatants or cell conditioned culture medium in the capture step of non-immunoglobulin proteins comprising at least one Ig-like domain, according to the invention can be derived from cells grown in the presence of serum such as fetal calf serum or horse serum, or grown in serum free medium.

"Cell-conditioned culture medium" denotes a nutrient medium in which cells have been cultured and which contains cell products.

When working with biological fluids containing cells, cell debris, and the like it is preferred to first filter and/or ultracentrifuge the fluid to remove these particulate contaminants.

The use of HCIC resin in the capture of non-immunoglobulin proteins comprising at least one Ig-like domain can be scaled up and advantageously combined with other purification and concentration techniques such as ion-exchange chromatography, ligand affinity chromatography, hydrophobic interaction chromatography, hydroxyapatite chromatography, ultrafiltration, and differential precipitation to obtain pure protein.

A large number of human and other mammalian proteins, including, for example, human growth hormone, human protein C clotting Factor VII and IL-18BP have been produced in host cells by transfecting these cells with DNA encoding these proteins and growing the recombinant cells and collecting the protein.

WO9909063 discloses the production of IL-18BP in mammalian cells in the application. Recombinant proteins can be produced also by transgenic animals and secreted into the milk.

Recombinant proteins are secreted by the cells into the cell culture medium (cell-conditioned culture medium), into the milk or are present in cell lysates and must be separated from other cell components, such as cell waste products, cell debris and proteins or other collected material.

The captured non-immunoglobulin Ig-like comprising proteins by MEP HYPERCEL® can be further purified by chromatographic separations. The following chromatographic separations are widely used: gel filtration (GF), ion exchange (IEX), and hydrophobic interaction (HI) chromatography, affinity chromatography and HPLC (high-performance liquid chromatography).

As described above, protein purification generally takes place in three phases: a capture step, in which the desired protein is isolated from a crude cell lysate or from cell culture medium; an intermediate step, in which proteins are isolated from contaminants similar in size or other physical/chemical properties; and finally a polishing step. Each purification stage has certain chromatography techniques and bead sizes that are best suited to a specific protein.

The intermediate step requires higher resolution for better separation of components. Generally, bead size correlates inversely with resolution; smaller bead sizes are thus more appropriate at this stage. Adsorptive techniques, such as IEX and HI, are generally used in these first two stages of purification. Gel filtration is usually reserved for the polishing step, in which a small, highly concentrated sample is applied to the column.

Two factors to consider when selecting a resin are its selectivity for the desired protein and its efficiency, as demonstrated by the peak width of eluting components. Selectivity refers to the ability of the resin to interact with and bind the protein of interest.

Resin efficiency refers to the ability of the chromatography matrix to elute components in distinct, rather than broad, peaks. High efficiency is essential when purifying closely eluting proteins; the combination of high selectivity and high efficiency yields high resolution.

Gel filtration (GF) (also called size-exclusion chromatography) separates globular proteins according to their molecular weights (Porath et al. 1959). GF can be performed under a variety of physical and chemical conditions and generally does not involve an elaborate protocol (Smith 1998, Amersham Biosciences A 1998). An aqueous solution of proteins is, with help of an eluent, passed through a solid phase or matrix composed of beads containing a range of pore sizes, chosen on the basis of the size of the target protein. The liquid volume "seen" by the column consists of a mobile phase (the liquid surrounding the beads, or "void volume") and a stationary phase (the liquid contained within the beads' pores).

Molecules that are too large to enter the bead pores will only come in contact with the void volume and will therefore elute first from the column. However, the smallest molecules will diffuse into the pores and come into contact with the total column volume and will elute last, with molecules of intermediate size eluting between the void volume and the total column volume.

One factor to consider when choosing a GF medium is the exclusion limit, or the molecular weight limit of the pores; proteins above this limit will be completely excluded from the pores and will not be separated. Some companies offer cross-linked resins, which are advantageous for high-pressure purifications because they do not compress and lose porosity under high-pressure conditions. GF has a number of advantages over other types of liquid chromatography. First, there is a high upper limit on the size of the proteins that can be purified using this technique; second the technique does not require the use of protein-denaturing organic solvents.

GF chromatography, however, can be difficult to fine-tune. In addition, protein resolution depends on the sample volume applied to the column. For example, dilute samples are difficult to purify by this technique. Finally, GF chromatography is not directly scalable from an analytical to a bulk purification level—two disadvantages for large-scale purification.

Ion Exchange Chromatography (IEX) offers a greater degree of control and specificity. IEX relies on charge interactions between the protein of interest and the ion exchange matrix, which is generally composed of resins, such as agarose, dextran, and cross-linked cellulose and agarose, that are covalently bound to a charged group (Amersham Biosciences B 1998).

Charged groups are classified according to type (cationic and anionic) and strength (strong or weak); the charge characteristics of strong ion exchange media do not change with pH, whereas with weak ion exchange media, sample loading capacity can change owing to loss of charge at varying pH, preventing protein binding (Amersham Biosciences B 1998). The most commonly used charged groups include diethylaminoethyl, a weakly anionic exchanger; carboxymethyl, a weakly cationic exchanger; quaternary ammonium, a strongly anionic exchanger; and methyl sulfonate, a strongly cationic exchanger. Other charged groups are available.

Ion exchange resins selectively bind proteins of opposite charge; that is, a negatively charged resin will bind proteins with a net positive charge, and vice-versa. The technique takes place in five steps: equilibration of the column to pH and ionic conditions ideal for target protein binding; reversible adsorption of the sample to the column through counterion displacement; introduction of elution conditions that change the buffer's pH or ionic strength in order to displace bound proteins; elution of substances from the column in order of binding strength (weakly-bound proteins are eluted first); and re-equilibration of the column for subsequent purifications. Researchers can design IEX protocols so that the target protein is selectively bound to the column (allowing contaminants to pass through) or so that contaminants adsorb and the target protein is selectively excluded (Amersham Biosciences B 1998).

Like GF chromatography, IEX is performed under aqueous conditions and requires no organic solvents. However, unlike GF, IEX allows a greater degree of specificity. Both the stationary phase (resin) and the mobile phase (buffer) can be tailored to meet purification needs. The buffer's pH and chemical composition can be controlled according to the properties of the protein of interest. One of IEX's main advantages is its scalability: IEX is directly upgradeable from a small-scale to a process-scale level. Furthermore, IEX resins are relatively inexpensive and widely available in bulk quantities.

Hydrophobic Interaction (HI) Chromatography relies on interactions between exposed hydrophobic patches on the protein's surface and hydrophobic ligands attached to the resin. The mechanism of hydrophobic adsorption is not well understood, and several theories exist to explain the process, all of which have at their core the increased structure of water molecules surrounding the protein-ligand complex (Amersham Biosciences 1993).

The HI process involves the use of a high salt buffer, which unravels the protein to expose hydrophobic sites. The protein is retained by the hydrophobic ligands on the column and is exposed to a gradient of buffers containing decreasing salt concentrations. As the salt concentration decreases, the protein returns to its native conformation and eventually elutes from the column.

The selectivity of HI resins depends on the structure of the hydrophobic ligand. Straight-chain alkyl ligands and aryl ligands are used, and in general, protein binding increases with increasing chain length (Amersham Biosciences 1993). The ideal resin choice depends on the target protein's chemistry. Finding the right hydrophobic ligand is an empirical process.

Non-immunoglobulin proteins comprising at least one Ig-like domain can be purified according to the invention with the MEP HYPERCEL® resin using as a starting material a fraction derived from another chromatographic separation step.

The term "purified" as used herein in reference to a polypeptide or protein does not refer only to absolute purity (such as a homogeneous preparation); instead, it refers to a polypeptide that is relatively purer than in the natural environment. Preferably, a polypeptide or protein is purified about 2-fold, about 3-fold, about 5-fold, about 10-fold, about 20-fold, about 50-fold, or about 100-fold. Most preferably, purification of at least one order of magnitude, preferably two or three orders, and more preferably four or five orders of magnitude is expressly contemplated.

Those skilled in the art will recognize that, with routine experimentation, the solutions, buffer composition, ionic strength, and pH can be adjusted as necessitated to improve the purification of non-immunoglobulin proteins comprising at least one Ig-like domain using HCIC resin such as MEP HYPERCEL®. For example, an important factor to consider when developing a protein purification procedure is the scalability of each individual step; many protocols are developed initially on a small-scale analytical level and then expanded to process-scale for bulk purification. Most types of resins including HCIC can be used for process-scale separations.

Although the procedure described above and in the following experimental example utilizes column chromatography, those skilled in the art will recognize that batch processing can also be utilized.

Having now described the invention, it will be more readily understood by reference to the following examples that are provided by way of illustration and are not intended to be limiting of the present invention.

EXAMPLES

Example 1

R-HIL-18BP Capture Step.

r-hIL-18BP was produced by a recombinant CHO clone in culture medium containing 2% serum. The r-hIL-18BP is a highly glycosylated and very acidic protein (isoelectric point of about 3).

MEP HYPERCEL® (BioSepra) is a Hydrophobic/Charge Induced Chromatography (HCIC) based resin. This resin is specially designed for the purification of antibodies (Boschetti et al. 2000 and Life Technologies Inc. 2000). At neutral pH, hydrophobic capture of antibody occurs by both an aliphatic-hydrophobic spacer and a neutral (uncharged) pyridine ring. When the pH is lowered thereafter (i.e. to pH 4), both the pyridine ring (pKa=4.8) in the ligand and the bound immunoglobulin (isoelectric point in the range of 6-6.5) become positively charged, resulting in charge repulsion and elution of the antibodies from the column. Because of the presence of the immunoglobulin-like (Ig-like) domain in IL-18BP, the possibility to capture IL-18BP with the MEP HYPERCEL® resin was examined.

The MEP HYPERCEL® column (5 ml resin) was pre-equilibrated with PBS pH 7.2 (at a flow rate of 3 ml/min). Concentrated crude material (CCM) containing r-hIL-18BP (0.5 mg/ml r-hIL-18BP and 32 mg/ml total protein) was loaded on the pre-equilibrated MEP HYPERCEL® column (at a flow rate of 1 ml/min). After loading, the column was first washed with PBS pH 7.2 until no protein was detected in the fractions emerging from the column (detection at A280) and then with the low pH buffer which is recommended by the manufacturer for the elution of immunoglobulins (50 mM acetate pH 4.5 buffer, at a flow rate of 3 ml/min). No IL-18BP was detected in the material collected from the column after the first wash (at pH 7.2) indicating that all the IL-18BP loaded was all bound to the column. A protein peak was detected after the low pH wash (FIG. 1, peak 1). The protein peak eluted by the low pH wash, which supposedly contains mainly immunoglobulins, did not contain any r-hIL-18BP (monitored by ELISA). The fact that IL-18BP is not eluted at pH 4.5 is since, in contrast to immunoglobulins, IL-18BP is highly acidic (isoelectric point of about 3) and pH of 4.5 is not acidic enough to induce IL-18BP to become positively charged (the protein is either not charged or is negatively charged). Therefore, in order to elute the IL-18BP from the column, propylene glycol, which can weaken hydrophobic interaction between proteins and is commonly used to stabilize the structure of proteins, was tested. First the column was washed with water for injection (WFI) and then with a solution of 35% propylene glycol (PG) (Merk, puris. Cat No. 107478) in 20 mM phosphate buffer at pH 8.4 (flow rate 1 ml/min). For the preparation of IL of phosphate buffer, 5.36 grams disodium hydrogen phosphate heptahydrate (MW 268.07 Merk, extra pure, cat NO. 106574) were dissolved in 0.8L WFI. The resulting solution was titrated to pH 8.4±0.2 with 6M HCL. After applying the PG solution to the column, a protein peak, peak 2 in FIG. 1 (detected at A280), was eluted from the column and was found to contain the r-hIL-18BP (detected by ELISA). Applying an additional elution step with a 50% PG solution did not result in further elution of proteins from the column.

The optimal concentration of propylene glycol required for the elution of r-hIL-18BP was evaluated using one the following schemes: A—a one step elution with 50% PG, B—a two step elution with first 35% PG and then 50% PG or C—a two step elution with first 25% PG and then 50% PG. The results summarized in Table 3 show that the recovery and purification factor were optimal using a solution of 35% PG in the elution step (Table 3).

Figure 2:
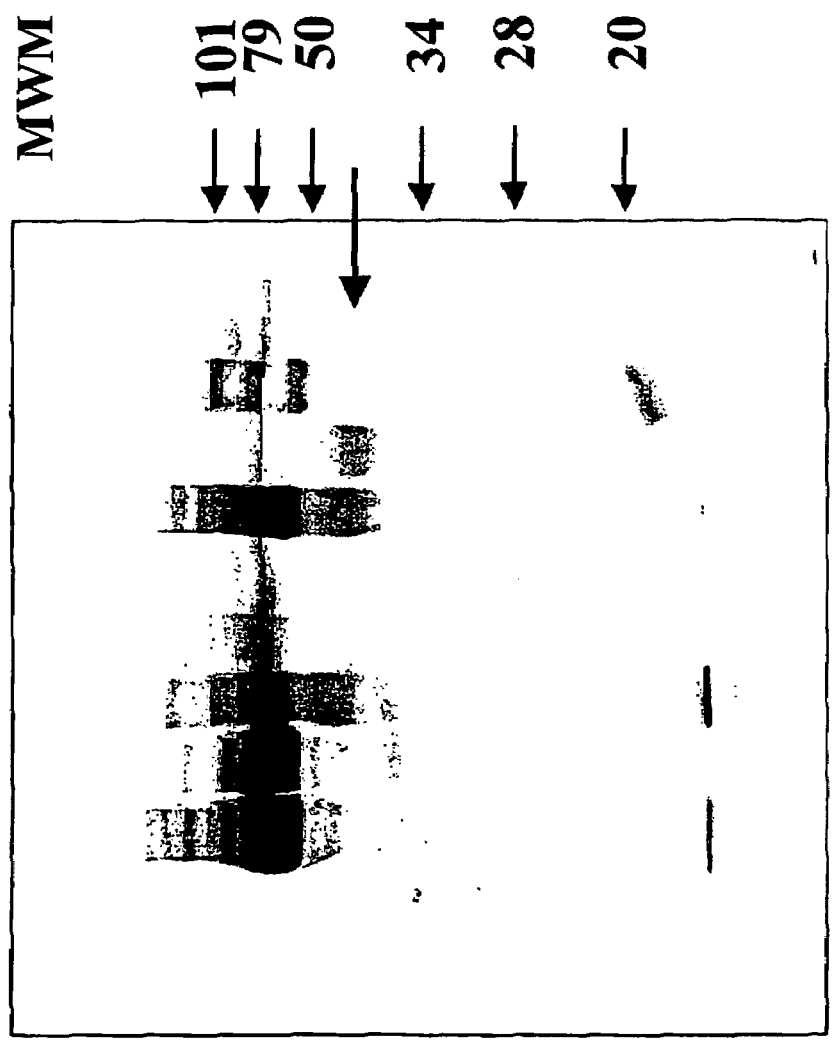
FIG. 2 shows the SDS-PAGE analysis of fractions obtained in the capture of IL-18BP using a MEP HYPERCEL® column. The resolved fractions are derived from the experiment shown in FIG. 1. Lanes 1) load, 2) unbound, 3) wash 50 mM acetate pH 4.5, 4) wash WFI, 5) elution peak 35% PG, 6) reference rhIL18BP, 7) MW markers. The long arrow points to the r-hIL-18BP band.

Thus, the capture of IL-18BP from CCM with the MEP HYPERCEL® resin resulted in increased purity (34%) and good recovery (85%). The purification factor was 22, and since the purified r-hIL-18BP fraction eluted in a relatively narrow peak (about 15 ml), the volumetric concentration factor increased to 1.7 fold (Table 3, FIG. 1). Fractions from different steps of the IL-18BP capture, e.g. loaded material, unbound fraction, the acidic wash fraction (50 mM acetate pH 4.5), the WFI wash fraction and the peak eluted with 35% PG, were analysed in SDS-PAGE (Example 5). The results obtained in the SDS-PAGE analysis (FIG. 2) are in line with the results obtained by ELISA over Bradford results (Table 3) and indicate that the protein peak fraction that eluted with 35% PG is highly enriched with r-hIL-18BP.

The high enrichment and purification factors observed (FIG. 2 line 5 eluted protein and line 6 IL-18BP reference protein) may be due to the selective binding of r-hIL-18BP to the MEP HYPERCEL® resin, probably trough the Ig-like domain, to the efficient wash step in acidic pH and to the selective elution conditions. Similar results of high enrichment and purification of IL-18BP were obtained when the material used for the capture is harvest of CHO cells growing and producing IL-18BP under SFM conditions (not shown).

TABLE 1

Purity, purification factor and concentration factor in the
Capture step of r-hIL-18BP using MEP HYPERCEL ®

| Experiment description | Load mg r-hIL-18BP/ml resin[b] | Recovery in elution (%)[b] | Purity (%)[c] | Purification Factor[d] | Conc. Factor |
|---|---|---|---|---|---|
| 1 step elution: | | | | | |
| 50% PG[a] | 3 | 60 | 18 | ×11 | ×1.5 |
| 2 step elution: | | | | | |
| 35% PG[a] | 3 | 85 | 34 | ×22 | ×1.7 |
| 50% PG[a] | | 0 | | | |
| 2 step elution: | | | | | |
| 25% PG[a] | 3 | 66 | 31 | ×20 | ×1.6 |
| 50% PG[a] | | 0 | | | |

[a]Propylene glycol concentrations in 20 mM phosphate buffer pH 8.4,
[b]Determined by ELISA for r-hIL 18-BP
[c]Purity = 100% × r-hIL-18BP (by ELISA)/Total protein (Bradford),
[d]The purification factor is calculated by dividing the purity of the elution fraction by the purity of the loaded fraction.

Example 2

Testing of Different MEP HYPERCEL® Resin Batches in r-hIL-18BP Capture.

To examine the batch-to-batch consistency of MEP HYPERCEL® resin performance, three different MEP HYPERCEL® resin batches were tested in the capture of r-hIL-18BP (batches #A112, #A113 and #A130). The parameters evaluated were a) resin capacity; b) purity; and c) purification factor. The columns (5 ml HR10 column, bed height 7 cm) were loaded with CMM at a concentration of IL-18BP of 2.5-3.5 mg r-hIL-18BP/ml resin (using the running conditions of Example 1).

The results in Table 2 show that runs with all three MEP HYPERCEL® resin batches yielded similar purity levels, purification factor and concentration factor of r-hIL-18BP. The column capacity was also similar in all the three resin batches (about 2 mg r-hIL-18BP/ml resin, Table 2).

TABLE 2

MEP HYPERCEL ® resin batch to batch consistency

| Resin batch number | Capacity mg r-hIL-18BP/ml resin[a,b] | Elution Volume (CV)[c] | r-hIL-18BP in elution fraction (mg) | Purity (%)[d] | Purification Factor[e] |
|---|---|---|---|---|---|
| MEP A112 | 2.4 | 3 | 9 | 40 | ×25 |
| MEP A113 | 2.4 | 3 | 9.5 | 43 | ×28 |
| MEP A130 | 2.1 | 3 | 10 | 36 | ×23 |

[a]Determined by ELISA for r-hIL 18-BP,
[b]Capacity = (Load − Unbound)/column volume,
[c]CV = Column volume = 5 ml,
[d]Purity of r-hIL-18BP by RP-HPLC,
[e]The purification factor is calculated by dividing the purity of the elution sample by the purity of r-hIL-18BP in the loaded sample.
Note:
the experimental error values of the ELISA and pre-developed HPLC methods were in the order of 10-20% and 5-10% respectively).

Example 3

Evaluation of Optimal pH for Loading of the Crude Material on the MEP HYPERCEL® Column for the Capture of IL-18BP.

The experimental capacity observed previously (Example 2) was in the range of 2.1-2.4 mg r-hIL-18BP/ml resin (Table 2). While immunoglobulins fractions start to elute from the column at pH 6.1 and are completely eluted from the column at pH 4 using the MEP HYPERCEL® column (Ref. 1 and 2), according to our preliminary experiments IL-18BP remains bound to the column at such a pH range. We reasoned that this characteristic could be exploited during loading of the CMM to the MEP-HYPERCEL® column to increase the capacity of the column for IL-18BP i.e. to allow less adsorption of immunoglobulins to the resin and consequently to permit more adsorption of r-hIL-18BP to the resin. Thus, the effect of loading CCM at pH 6.1 instead of pH 7.2 was investigated. The pH of the CCM containing the r-hIL-18BP was adjusted to pH 6.1 prior to application into the MEP HYPERCEL® column. Also, prior to loading, the column was equilibrated with buffer PBS pH 6.1, and after loading the first wash was carried out with the same buffer.

In previous experiments, the concentration of r-hIL18BP loaded was about 2 mg/ml resin and, in order to increase the concentration of r-hIL18-BP in the column to about 6 mg/ml resin, the volume of CCM loaded into the column was augmented.

Figure 3:
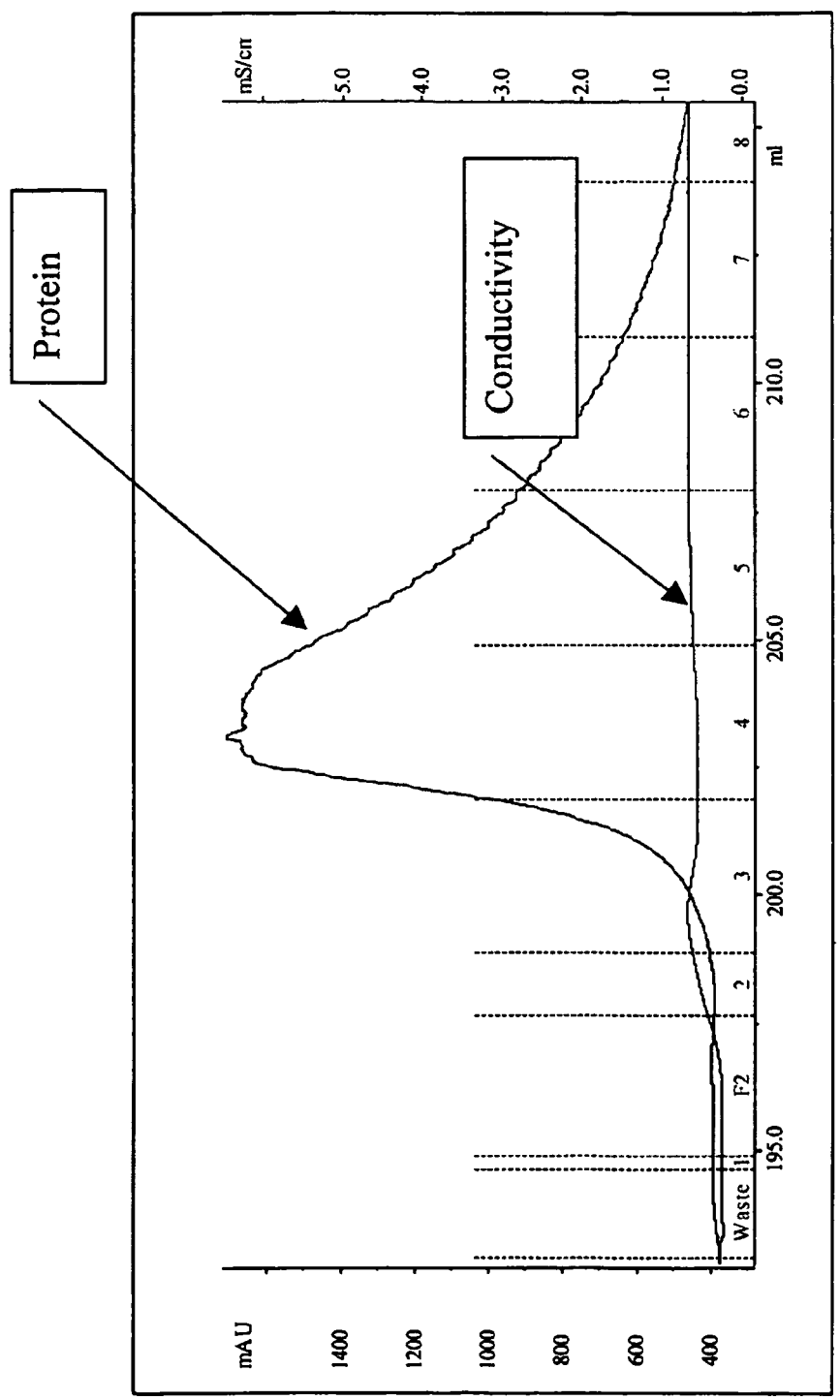
FIG. 3 shows the chromatogram of the fractionation of the r-hIL-18BP elution peak in a MEP HYPERCEL® column.
Run Data: Column bed volume: 5 ml.
Equilibration buffer: PBS pH 6.1—flow rate 3 ml/min.
Load: CCM CH008 titrated to pH 6.1—flow rate 3 ml/min.
Washes: 1) PBS pH 6.1, 2) 50 mM acetate pH 4.1, 3) WFI—flow rates of all washes 3 ml/min.
Elution: 35% propylene glycol in 20 mM phosphate buffer at pH 8.4—flow rate 1 ml/min. The figure shows the expansion of the elution peak, collected in 3 ml fractions. The left ordinate indicates absorption at A280, the right ordinate indicates conductivity (mS/crr units), in the abscissa is denoted the volume flowing trough the column (ml).
The left ordinate indicates absorption at A280 (protein mAU units), the right ordinate indicates conductivity (mS/crr units) in the abscissa is denoted the volume flowing through the column (ml).

The results summarized in Table 3 show that the capacity of the resin for IL-18BP increased at least by two-fold when loading CCM at pH 6.1 as compared to the capacity observed when loading at pH 7.2 (Table 3). Since the IL-18BP is eluted in a narrow peak (see in FIG. 3, 5 fractions of 3 ml each), the concentration factor increased by two-fold.

These results demonstrate that loading CCM at pH 6.1 results in increased capacity and increased concentration of the eluted IL-18BP.

TABLE 3

Effect of pH on r-hIL-18BP Capture on the MEP HYPERCEL ® resin

| pH of CCM[a] | Load mg r-hIL-18BP/ml resin[b] | Capacity mg r-hIL-18BP/ml resin[c] | r-hIL 18BP in elution fraction (mg)[b] | Purity (%)[d] | Purification Factor[e] | Conc. Factor |
|---|---|---|---|---|---|---|
| pH 7.2 | 2.5 | 2.4 | 9 | 40 | ×25 | ×1.2 |
| pH 7.2 | 3.5 | 2.1 | 10 | 36 | ×23 | ×1.3 |
| pH 6.1[a] | 5.8 | 5.1 | 24.6 | 36 | ×23 | ×3.1 |
| pH 6.1[a] | 6.2 | 5.3 | 26.6 | 33 | ×21 | ×2.6 |

[a]the CCM was titrated to pH 6.1 with 1 M sodium di-hydrogen phosphate before loading,
[b]Determined by ELISA for r-hIL 18-BP,
[c]Capacity = (Load − Unbound)/column volume,
[d]Purity of r-hIL-18BP by RP-HPLC,
[e]The purification factor is calculated by dividing the purity of the elution sample by the purity of r-hIL-18BP in the loaded sample.
Note:
the experimental error values of the ELISA were in the order of 10-20%.

Example 4

Effect of the Loading Rate on r-hIL-18BP Capture Using the MEP HYPERCEL® Column.

The loading velocity of the crude material on the column can effect the capture performance of the column, for example, fast loading is more convenient for operation, while slow loading may lead to increase in yield. Thus, the effect of the loading flow rate on the capture of r-IL-18BP in the MEP HYPERCEL® column was evaluated. The column was loaded with CMM in order to get 6 mg r-hIL-18BP/ml resin (see previous example). The CCM was loaded at a flow rate of 0.5 ml/min. in one experiment, at 3 ml/min. in a second experiment (Table 4) and compared to the standard flow rate of 1 ml/min. At the flow rate of 3 ml/min. there was a substantial decrease in r-hIL-18BP recovered in the elution fraction in comparison to that recovered at the flow rate of 1 ml/min. The loading at flow rate of 0.5 ml/min. rate did not significantly increase the amount of r-hIL-18BP in the elution fraction in comparison to loading at flow rate of 1 ml/min.

TABLE 4

Effect of loading flow on r-hIL-18BP recovered in elution fraction

| Flow rate | Linear flow rate (cm/h) | r-hIL-18BP in elution fraction (mg)[c] | Purity (%)[c] | Purification factor[d] | Conc. factor |
|---|---|---|---|---|---|
| 0.5 ml/min CH-008[a] | 37.5 | 21 | 44 | ×28 | ×2.9 |
| 1 ml/min CH-008[a] | 75 | 19.5 | 33 | ×21 | ×2.6 |
| 3 ml/min CH-009[a] | 225 | 13.5 | 45 | ×30 | ×1.5 |

[a]the CCM was titrated to pH 6.1 with 1 M sodium di-hydrogen phosphate,
[b]By ELISA for r-hIL 18-BP,
[c]Purity of r-hIL-18BP by RP-HPLC,
[d]The purification factor is calculated by dividing the purity of the elution sample by the percentage of r-hIL-18BP in the loaded sample.

Example 5

SDS-PAGE Analysis

Five µg of purified r-hIL-18BP or 20 µl of chromatography fractions were diluted in sample buffer 4:1. Samples were incubated for 5 min. at 95° C. and separated on a Tris-Glycine-12% SDS-PAGE ready gel under reducing or non-reducing condition. The gels were run at 20 mA constant current for ~1.5 hr and stained with Coomassie blue or GELCODE staining.

Sample buffer×4; 4 gr. SDS (3.1.16), 20 gr. sucrose (3.1.32), 0.8 M DTT (3.1.31) and 20 mg bromophenol blue (3.1.33) in 50 ml 0.15 M Tris pH 6.8 (3.2.15 diluted 1:13.3 with WFI adjusted to pH 6.8).

Running Buffer×10; 15 gr. Tris-HCl (4.2.66), 72 gr. Glycine (4.2.29), 5 gr. SDS (3.1.16) in 500 ml water (7.10) pH 8.3.

Example 6

ELISA for Detection of r-hIL-18BP

Microtiter plates were coated with 5 µg/ml monoclonal antibody prepared against IL-18BP (monoclonals prepared as described in WO02092008 and affinity purified on a Protein G column) in coating buffer overnight at 4° C. The plates were washed three times with washing buffer and blocked with blocking buffer (see below). After washing, 100 µl r-hIL-18BP sample aliquots were added to the wells and incubated for 1 hour at 37° C. with shaking. Plates were washed again, and 100 µl of rabbit antiserum, diluted 1:5,000 in assay buffer were added to each well. After 1-hour incubation at 37° C. with shaking the washing procedure was repeated and bound antibodies were detected with HRP conjugated with goat anti-rabbit diluted 1:10,000 in assay buffer. 100 l/well HRP-conjugate were added to the plates and incubated for 1 hour at 37° C. with shaking. The plates were then washed and the colour reaction was developed by adding 125 µl/well OPD substrate solution. The reaction was stopped by adding 125 µl/well of 4N HCl. The absorbance was measured at 492 nm in an ELISA reader. A sample from a batch of immunopurified r-hIL-18BP-His was used as reference sample during the development of the assay. The protein content of the immunopurified reference standard was determined by spectroscopy at A280 using an extinction coefficient of 1.26 OD/mg. The calibration curve was prepared by serial dilutions of the standard r-hIL-18BP to give a range from 20 ng/ml to 0.3 ng/ml in assay buffer for each assay.

Blocking buffer—BSA Diluent/Blocking solution concentrate (3.1.50) diluted 1:10.

Assay buffer—BSA Diluent/Blocking solution concentrate (3.1.50) diluted 1:15.

Example 7

Reverse Phase HPLC (RP-HPLC) Analysis

Identity and purity of r-hIL-18BP fractions were analysed on a RP-HPLC (RP-HPLC Column Supelcosil LC308 Cat No. 5810, 4.6 mm IDX5 cm, Lot # C175, Supelco (USA)) column as follows: 20 µg of r-hIL-18BP were injected into the column and separated using a gradient of 10-100% n-Propanol in 0.1% TFA (Trifluoroacetic Acid, Baker Cat. No. 9470-01).

Example 8

Capture of r-IL6-IL6R Chimera by MEP HYPERCEL® Column.

IL6-IL6R chimera (also called "IL6R/IL6" or "IL-6 chimera"), is a chimeric molecule comprised of the soluble part of the interleukin-6 receptor, bearing the Ig-like domain, fused to interleukin-6 (Chebath et al. 1997 and Kollet et al. 1999). The binding of r-hIL6-IL6R chimera to MEP HYPERCEL® column was explored. The material used for loading was crude harvest of CHO producer cells in 2% FBS obtained after clarification and 20 fold concentration by a 10 kDa membrane (CCM).

The crude harvest (CCM) of r-hIL6-IL6R chimera produced in CHO cells was loaded onto the column of MEP HYPERCEL® (Life technologies Cat. No 12035), equilibrated with PBS. After wash of the column with PBS the captured material was eluted with 2-5 column bed volumes of 20 mM Na-phosphate buffer pH 8.4 containing 35% propylene glycol (PG). Loading and elution conditions were similar as for r-hIL-18BP capture process (see below). The amount of protein in the eluted fraction was analyzed by ELISA and/or by SDS-PAGE.

Figure 4:
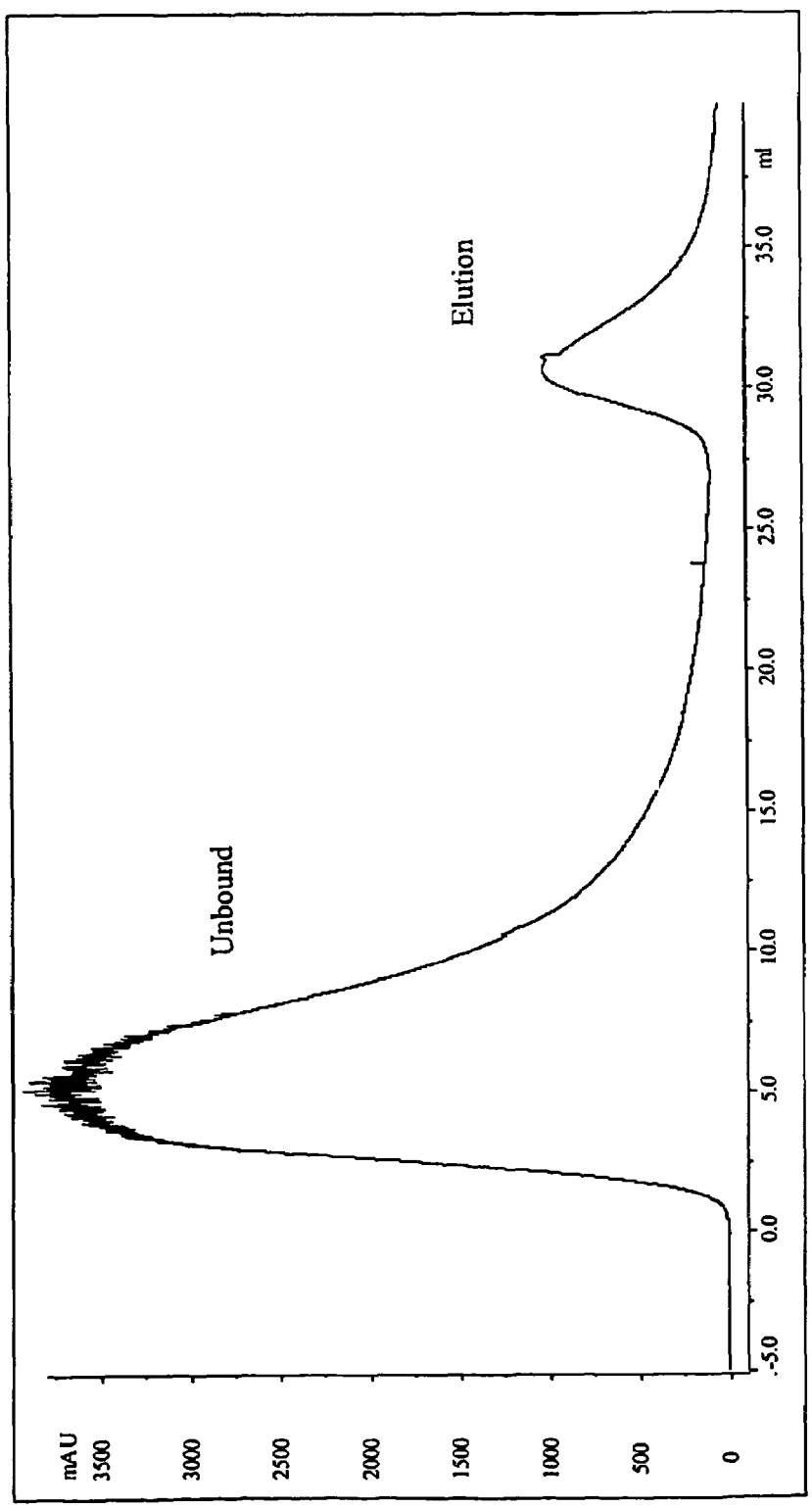
FIG. 4 shows a chromatogram of r-hIL6-IL6R capture on a MEP-HYPERCEL® column.
Run Data: Column bed volume: 1 ml.
Equilibration buffer: PBS—flow rate 1 ml/min.
Load: crude harvest containing 0.81 mg/ml r-hIL6-IL6R (ELISA)—flow rate 0.5 ml/min.
Wash: PBS—flow rate 0.5 ml/min.
Elution: 35% propylene glycol in 20 mM phosphate buffer at pH 8.4—flow rate 0.5 ml/min. Detection at A280.
The left ordinate indicates absorption at A280 (protein mAU units), the right ordinate indicates conductivity (mS/crr units) in the abscissa is denoted the volume flowing through the column (ml).
Figure 5:
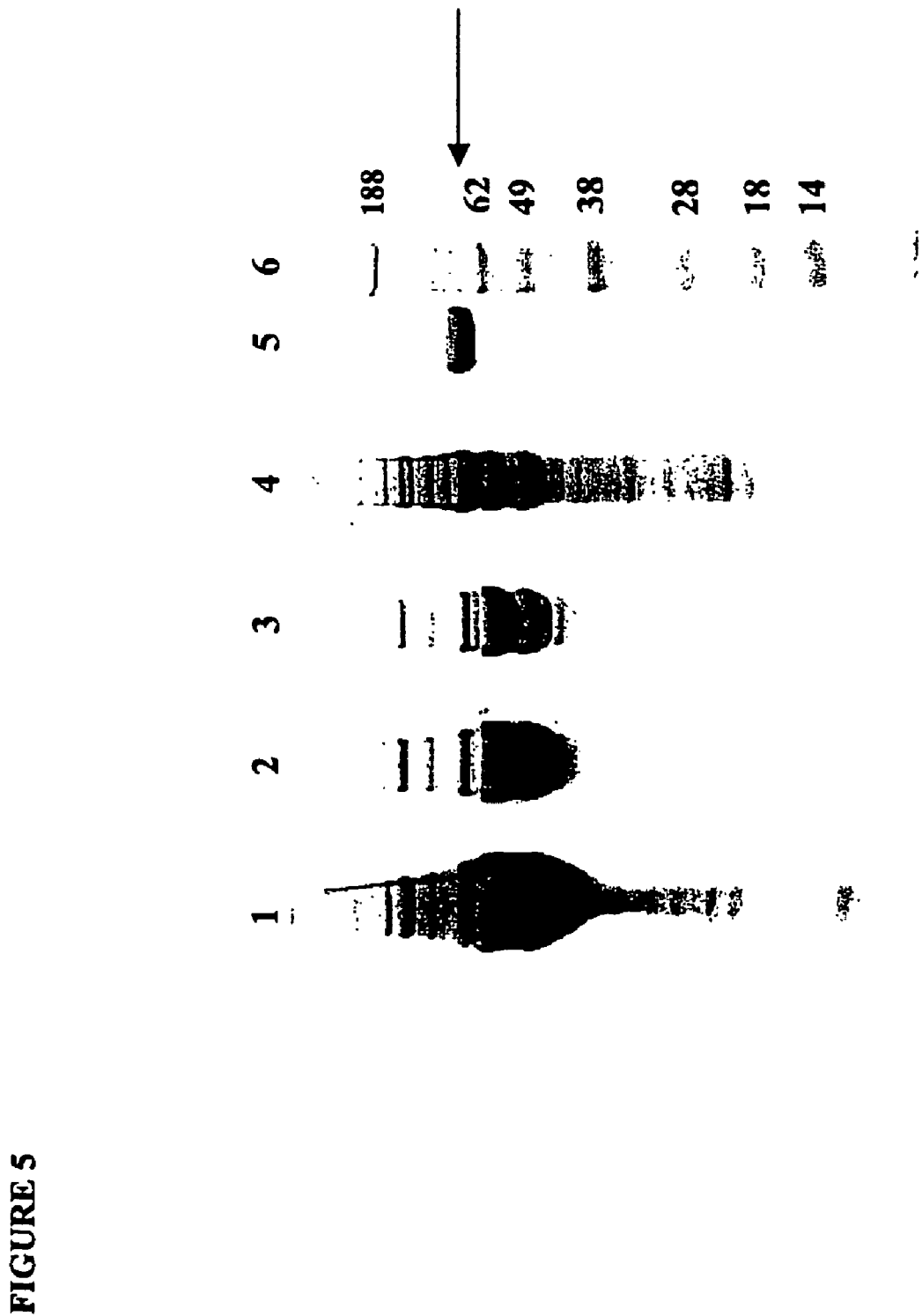
FIG. 5 shows the SDS-PAGE analysis of load and elution fractions from MEP HYPERCEL® column loaded with r-hIL6-IL6R chimera in FBS containing crude harvest.
The fractions were loaded on the gel—20 mcg/lane. Lanes 1)—load, 2) and 3)—unbound material, 4)—elution peak by 35% PG, 5) purified reference r-hIL6-IL6R, 5 mcg/lane, 6) molecular weight (MW) markers. The arrow points to the r-hIL6-IL6R band.

More specifically, a 1 ml column was equilibrated with 20 ml of PBS and loaded with 4 ml of r-hIL6-IL6R chimera crude harvest. The flow rate employed was 0.5 ml/min. The column was washed by 20 ml of PBS and the bound material was eluted with elution buffer containing 35% propylene glycol in 20 mM phosphate pH 8.4. The chromatography profile is shown in FIG. 4. The unbound and eluted fractions were collected and analysed by ELISA and SDS-PAGE. The gel stained by Coomassie blue is depicted in FIG. 5.

Table 5 summarizes the chromatography results.

TABLE 5

Capture and elution of r-hIL6-IL6R chimera on MEP HYPERCEL® column

| Fractions | Volume (ml) | Total r-hIL6 Chimera by ELISA (mg) | Total protein by Bradford (mg) | Relative concentration (r-1L6 Chimera*/total protein**) | Purification (Fold) | Yield (%) |
|---|---|---|---|---|---|---|
| Load | 4 | 3.24 | 1384 | $2.34 \times 10^{-3}$ | 1 | |
| Unbound | 13.5 | 0.31 | 162 | $1.9 \times 10^{-3}$ | | 9.7 |
| Elution | 6 | 2.34 | 10.8 | $220 \times 10^{-3}$ | 94 | 72.2 |

*By ELISA
**By Bradford

These conditions result in a capacity is above 2 mg r-hIL6-IL6R per ml resin, yield around 72% and purification factor of about 94 fold.

The results show that the r-hIL6-IL6R chimera, which was essentially undetectable in the crude harvest (FIG. 5), appeared as one of the major bands in the eluted fraction (94 fold purification by ELISA).

The MEP HYPERCEL® was found to be a suitable resin for the r-hIL6-IL6R capture.

In order to evaluate the contribution of the Ig-like domain of r-hIL6-IL6R chimera in binding to the MEP HypercCel column, the crude harvest of CHO cells producing IL-6 was loaded into the MEP HYPERCEL® column under similar conditions as the intact r-hIL6-IL6R chimera. It was found that the IL-6, lacking the Ig-like domain, did not bind to the column MEP HYPERCEL® column. This result indicates that the Ig-like domain is essential for the capture by MEP HYPERCEL® column.

Example 9

Capture of r-beta-galactosidase by MEP HYPERCEL® Column.

Figure 6:
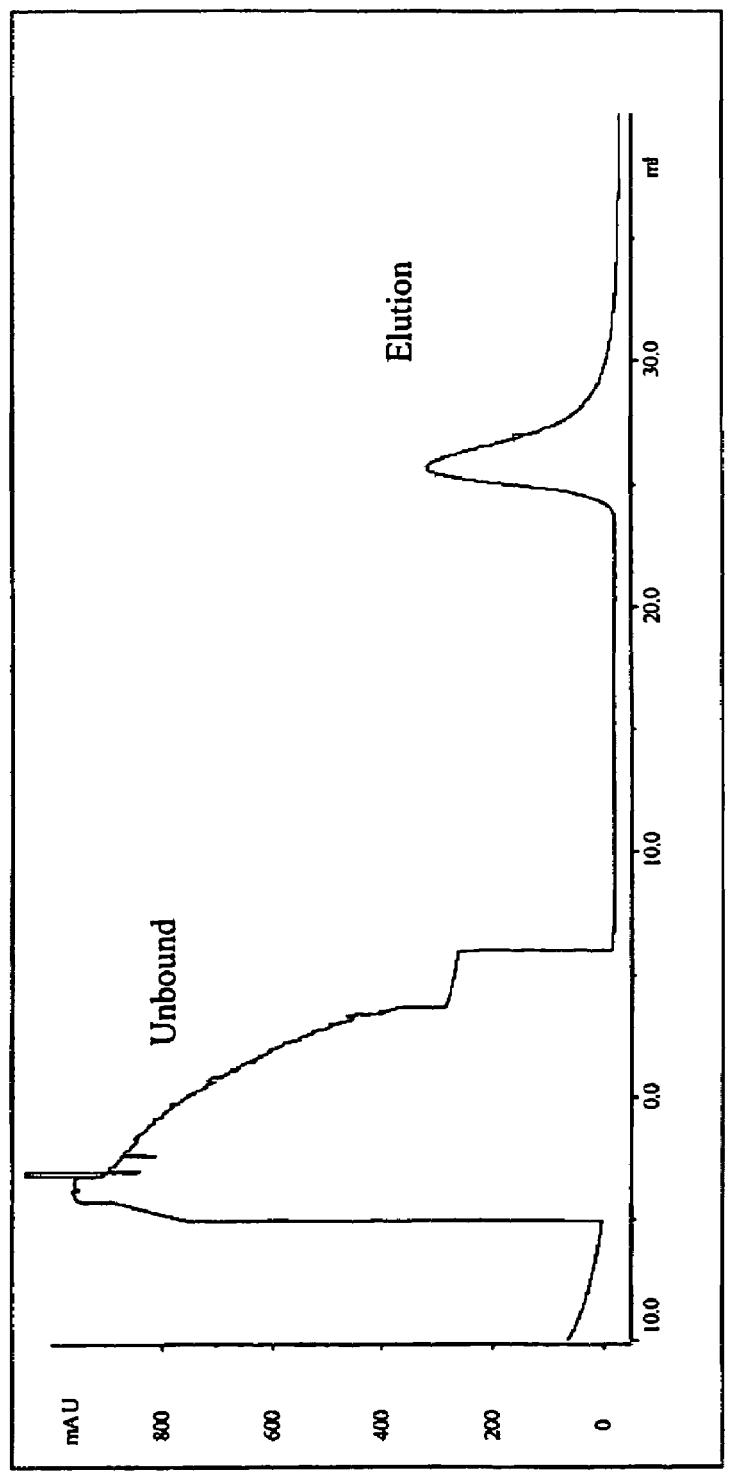
FIG. 6 shows a chromatogram of beta-galactosidase capture on a MEP-HYPERCEL® column.
Run Data: Column bed volume: 1 ml.
Equilibration buffer: PBS—flow rate 1 ml/min.
Load: serum free medium (SFM) containing 0.625 mg/ml beta-galactosidase—flow rate 0.5 ml/min.
Wash: PBS—flow rate 0.5 ml/min. Elution: 35% propylene glycol in 20 mM phosphate buffer at pH 8.4—flow rate 0.5 ml/min. Detection at A280.
The left ordinate indicates absorption at A280 (protein mAU units), the right ordinate indicates conductivity (mS/crr units) in the abscissa is denoted the volume flowing through the column (ml).
Figure 7:
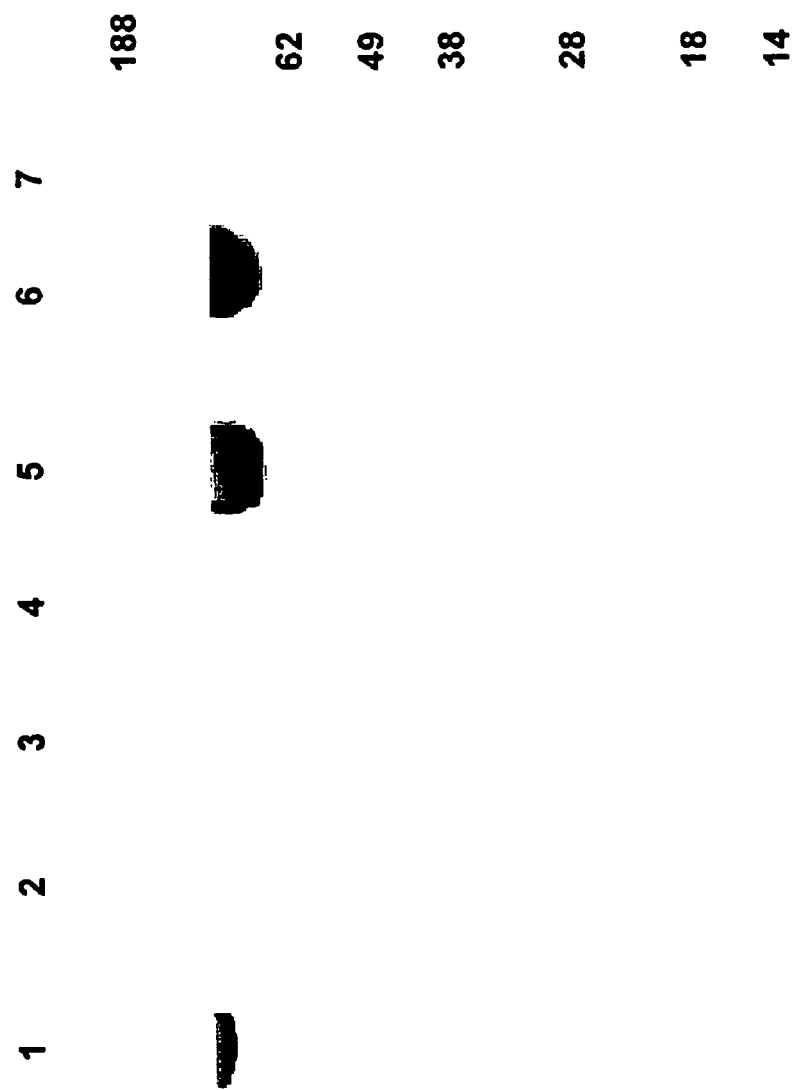
FIG. 7 shows the SDS-PAGE analysis of load and elution fractions from a MEP HYPERCEL® column loaded with beta-galagalactosidase in SFM (ProCHO5).
The fractions were loaded on the gel according total protein—20 mcg/lane. Lanes 1) load, 2)-4) unbound, 5) elution peak 35% PG, 6) purified reference beta-galactosidase, 5 mcg/lane 7) MW markers.

In another experiment the binding of the bacterial protein having an Ig-like domain, beta-galactosidase, to MEP HYPERCEL® column was examined. E. coli beta-galactosidase (Roche Diagnostic, Cat No. 567779) was spiked in serum free medium (SFM) ProCHO-5 at a concentration 0.625 mcg/ml One ml column equilibrated with 20 ml of PBS was loaded with 4 ml of beta-galactosidase in SFM. The flow rate employed was 0.5 ml/min. The column was washed by 20 ml of PBS and the bound material was eluted using elution buffer containing 35% propylene glycol in 20 mM phosphate pH 8.4. The chromatography profile is shown in FIG. 6. The unbound and eluted fractions were collected and analysed by SDS-PAGE. The gel presented on FIG. 7 containing different fractions of the chromatographic separation, the reference material and molecular weight markers is stained with Coomassie blue. The results show that the beta-galactosidase efficiently binds to the MEP-HYPERCEL® column and that the beta-galactosidase protein is efficiently eluted from the column by 35% PG.

Therefore MEP HYPERCEL® column is suitable for the purification of b-galactosidase.

REFERENCES

C. Smith, "Liquid chromatography: Products in the protein chemist's tool chest," The scientist 12[16]:14, Mar. 16, 1998.

Amersham Biosciences, "Gel filtration. Principles and methods," 1998.

J. Porath, P. Flodin, "Gel filtration: Method for desalting and group separation," Nature, 183:1657-1659, 1959.

Amersham Biosciences, "Ion exchange chromatography. Principles and methods."

Amersham Biosciences, "Hydrophobic interaction chromatography. Principles and methods," 1993.

Constans (2001) "protein purification I: Liquid chromatography" The Scientist 16[2]:40

Boschetti, E. et. Al. "Hydrophobic Charge-Induced Chromatography" Genetic Engineering, Vol 20(13) July 2000.

MEP HYPERCEL® product instructions: Life technologies. Inc. 2000.

Anderson, D. M., Maraskovsky, E., Billingsley, W. L., Dougall, W. C., Tometsko, M. E., Roux, E. R., Teepe, M. C., DuBose, R. F, Cosman, D., Galibert, L. (1997) "A. homologue of the TNF receptor and its ligand enhance T-cell growth and dendritic-cell function." Nature, 390, 175-179.

Bazan, J. F., Timans, J. C. and Kaselein, R. A. (1996) "A newly defined interleukin-1?" Nature 379, 591.

Chebath J, Fischer D, Kumar A, Oh J W, Kolett O, Lapidot T, Fischer M, Rose-John S, Nagler A, Slavin S, Revel M. Eur Cytokine Netw 1997 December; 8(4):359-65 Interleukin-6 receptor-interleukin-6 fusion proteins with enhanced interleukin-6 type pleiotropic activities.

Engelmann, H., Aderka, D., Rubinstein, M., Rotman, D. and Wallach. D. (1989) "A tumor necrosis factor-binding protein purified to homogeneity from human urine protects cells from tumor necrosis factor toxicity" J. Biol. Chem. 264, 11974-11980.

Engelmann, H., Novick, D. and Wallach, D. (1990) "Two tumor necrosis factor-binding proteins purified from human urine. Evidence for immunological cross-reactivity with cell surface tumor necrosis factor receptors." J. Biol. Chem. 265, 1531-1536.

Ghayur, T., Banerjee, S., Hugunin, M., Butler, D., Herzog, L., Carter, A., Quintal, L., Sekut, L., Talanian, R., Paskind, M., Wong, W., Kamen, R., Tracey, D., and Allen, H. (1997) "Caspase-1 processes IFN-gamma-inducing factor and regulates LPS-induced IFN-gamma production." Nature 386, 619-623.

Gu, Y., Kuida, K., Tsutsui, H., Ku, G., Hsiao, K., Fleming, M. A., Hayashi, N., Higashino, K., Okamura, H., Nakanishi, K., Kurimoto, M., Tanimoto, T., Flavell, R. A., Sato, V., Halaby et al. (1998) J. Mol. Evol. 46389-400.

Halaby et al. (1999) Protein Engineering vol. 12 n0 7 563-571.

Heinrich P C, Behrmann I, Muller-Newen G, Schaper F, Graeve L. Interleukin-6-type cytokine signalling through the gp130/Jak/STAT pathway. Biochem J. 1998 Sep. 1; 334 2:297-314. Review.

Higashio, K. (1998) "Identity of osteoclastogenesis inhibitory factor (OCIF) and osteoprotegerin (OPG): a mechanism by which OPG/OCIF inhibits osteoclastogenesis in vitro." Endocrinology, 139, 1329-37.

Jones S A, Horiuchi S, Topley N, Yamamoto N, Fuller G M. The soluble interleukin 6 receptor: mechanisms of production and implications in disease. FASEB J. 2001 January; 15(1):43-58. Review.

Kim, S. H., Eisenstein, M., Reznikov, L., Fantuzzi, G., Novick, D., Rubinstein, M. and Dinarello, C. A. (2000) "Structural requirements of six naturally occurring isoforms of the IL-18 binding protein to inhibit IL-18." Proc Natl Acad Sci USA 97, 1190-5.

Kim, S. H., Reznikov, L. L., Stuyt, R. J., Selzman, C. H., Fantuzzi, G., Hoshino, T., Young, H. A. and Dinarello, C.

A. (2001) "Functional reconstitution and regulation of IL-18 activity by the IL-18R beta chain." J Immunol 166, 148-54.

Kollet O, Aviram R, Chebath J, ben-Hur H, Nagler A, Shultz L, Revel M, Lapidot T.

The soluble interleukin-6 (IL-6) receptor/IL-6 fusion protein enhances in vitro maintenance and proliferation of human CD34(+)CD38(-/low) cells capable of repopulating severe combined immunodeficiency mice. Blood. 1999 Aug. 1; 94(3):923-31.

McMahan et al. (1991) "A novel IL-1 receptor, cloned from B cells by mammalian expression, is expressed in many cell types." EMBO J. 10(10):2821-32.

Muhl, H., Kampfer, H., Bosmann, M., Frank, S., Radeke, H. and Pfeilschifter J. (2000) "Interferon-gamma mediates gene expression of IL-18 binding protein in nonleukocytic cells." Biochem Biophys Res Commun January 267, 960-3.

Nakamura, K., Okamura, H., Wada, M., Nagata, K. and Tamura, T. (1989). "Endotoxin-induced serum factor that stimulates gamma interferon production." Infect-Immun 57, 590-5 issn: 0019-9567.

Nakamura, K., Okamura, H., Nagata, K., Komatsu, T. and Tamura, T. (1993) "Purification of a factor which provides a costimulatory signal for gamma interferon production." Infect. Immun. 61, 64-70.

Nakamura, S., Otani, T., Ijiri, Y., otoda, R., Kurimoto, M. and Orita, K. (2000)" IFN-γ-dependent and -independent mechanisms in adverse effects caused by concomitant administration of IL-18 and IL-12. The journal of Immunology 164, 3330-6.

Novick, D., Engelmann, H., Wallach, D. and Rubinstein. M. (1989) "Soluble cytokine receptors are present in normal human urine." J. Exp. Med. 170, 1409-14.

Novick, D., Cohen, B. and Rubinstein, M. (1992) "Soluble Interferon-alpha Receptor Molecules Are Present in Body Fluids." FEBS Lett 314, 445-8.

Novick, D., Cohen, B. and Rubinstein, M. (1994) "The Human Interferon alpha/beta Receptor—Characterization and Molecular Cloning." Cell 77, 391-400.

Novick, D., Kim, S., Fantuzzi, G., Reznikov, L. L., Dinarello, C. A. and Rubinstein, M. (1999) "Interleukin-18 Binding Protein: A Novel Modulator of the Th1 Cytokine Response. Immunity 10, 127, 36.

Okamura, H., Tsutsui, H., Komatsu, T., Yutsudo, M., Hakura, A., Tanimoto, T., Torigoe, K., Okura, T., Nukada, Y., Hattori, K., Akita, K., Namba, M., Tanabe, F., Konishi, K., Fukuda, S., and Kurimoto, M. (1995) "Cloning of a new cytokine that induces IFN-gamma production by T cells." Nature 378, 88-91.

Okamura, H., Kashiwamura, S., Tsutsui, H., Yoshimoto, T. and Nakanishi, K. (1998) "Regulation of IFN-γ production by IL-12 and IL-18" Current Opinion in Immunology. 10, 259-264.

Osborn et al. (1994) "Arrangement of domains, and amino acid residues required for binding of vascular cell adhesion molecule-1 to its counter-receptor VLA-4 (alpha 4 beta 1)." J Cell Biol February; 124(4):601-8

Pedersen B K, Steensberg A, Schjerling P. Muscle-derived interleukin-6: possible biological effects. J. Physiol. 2001 Oct. 15; 536(Pt 2):329-37. Review.

Puren, A. J., Fantuzzi, G., Dinarello, C. A. (1999) "Gene expression, synthesis, and secretion of interleukin 18 and interleukin 1beta are differentially regulated in human blood mononuclear cells and mouse spleen cells." Proc Natl Acad Sci USA, 96, 2256-61.

Schwartz et al. (2001) "Comparison of hydrophobic charge induction chromatography with affinity chromatography on protein A for harvest and purification of antibodies." Journal of Chromatography A 908 251-263.

Simonet, W. S., Lacey, D. L., Dunstan, C. R., Kelley, M., Chang, M. S., Luthy, R., Nguyen, H. Q., Wooden, S., Bennett, L., Boone, T., Shimamoto, G., DeRose, M., Elliott, R., Colombero, A., Tan, H. L., Trail, G., Sullivan, J., Davy, E., Bucay, N., Renshaw-Gegg, L., Hughes, T. M., Hill, D., Pattison, W., Campbell, P., Boyle, W. J. (1997). "Osteoprotegerin: a novel secreted protein involved in the regulation of bone density". Cell, 89, 309-19.

Tsutsui, H., K. Nakanishi, K. Matsui, K. Higashino, H. Okamura, Y. Miyazawa, and K. Kaneda. (1996) "IFN-gamma-inducing factor up-regulates Fas ligand-mediated cytotoxic activity of murine natural killer cell clones". J. Immunol. 157, 3967-73 issn: 0022-1767.

Urushihara, N., Iwagaki, H., Yagi, T., Kohka, H., Kobashi, K., Morimoto, Y., Yoshino, T., Tanimoto, T., Kurimoto, M., Tanaka, N. (2000) "Elevation of serum interleukin-18 levels and activation of Kupffer cells in biliary atresia." J Pediatr Surg 35, 446-9.

Ushio, S., Namba, M., Okura, T., Hattori, K., Nukada, Y., Akita, K., Tanabe, F., Konishi, K., Micallef, M., Fujii, M., Torigoe, K., Tanimoto, T., Fukuda, S., Ikeda, M., Okamura, H., and Kurimoto, M. (1996) "Cloning of the cDNA for human IFN-gamma-inducing factor, expression in *Escherichia coli*, and studies on the biologic activities of the protein." J. Immunol. 156, 4274-9.

Vigers, G. P., Anderson, L. J., Caffes, P., Brandhuber, B. J. (1997) "Crystal structure of the type-I interleukin-1 receptor complexed with interleukin-1beta." Nature 386, 190-4.

Wiesmann C et al. (2000) "Ligand-binding sites in Ig-like domains of receptor tyrosine kinases" J Mol Med 78(5): 247-60.

Xiang, Y. and Moss, B. (1999) "Identification of human and mouse homologs of the MC51L-53L-54L family of secreted glycoproteins encoded by the Molluscum contagiosum poxvirus." Virology 257, 297-302.

Yasuda, H., Shima, N., Nakagawa, N., Mochizuki, S. I., Yano, K., Fujise, N., Sato, Y., Goto, M., Yamaguchi, K., Kuriyama, M., Kanno, T., Murakami, A., Tsuda, E., Morinaga, T, and Higashio, K., (1998) "Identity of Osteoclastogenesis Inhibitory Factor (OCIF) and Osteoprotegerin (OPG): A Mechanism by which OPG/OCIF Inhibits Osteoclastogenesis in Vitro*" Endocrinology 139(3): 1329-1337.

The invention claimed is:

1. A method for purifying or capturing a non-immunoglobulin protein of interest having between one and ten immunoglobulin-like (Ig-like) domains from a biological fluid, comprising the steps of:
    a) contacting the biological fluid containing the protein of interest with a Hydrophobic Charge Induction Chromatography (HCIC) resin, wherein the HCIC resin comprises a mercapto-ethyl pyridine ligand,
    b) washing out the resin with a buffer to remove unbound contaminants, and
    c) eluting the protein of interest by treating the resin with a buffer solution comprising an organic solvent, wherein the organic solvent is isopropyl alcohol, propylene glycol and/or polyalcohols.

2. The method according to claims 1, wherein the organic solvent used in step c) is propylene glycol.

3. The method according to claim 2, wherein the concentration of propylene glycol in the solution is between about 25 and 50%.

4. The method according to claim 1, wherein step a) is carried out at acidic pH.

5. The method according to claim 4, wherein the pH used is between about 3 and 6.8.

6. The method according to claim 1, wherein the washing of step b) is carried out with a buffer solution having an acidic pH.

7. The method according to claim 6, wherein the pH used is between about 3 and 6.8.

8. The method according to claim 1, wherein the biological fluid is selected from a cell-conditioned culture medium, cell lysate, cell extract, tissue extract, blood plasma, serum, milk, urine, ascites, cerebrospinal fluid, vegetable juice, plant extracts or a fraction obtained from an earlier chromatographic separation step.

9. The method according to claim 1, wherein the protein of interest has 1 to 7 Ig-like domains.

10. The method according to claim 1, wherein the protein of interest is selected from IL-18 binding protein (IL-18BP), NCAM, Fibronectin type III, ICAM-1, mad CAM-1, PE CAM-1, VCAM-1, titin, cadherin, neurocan, LIFR, CNTFR, IL-1R, IL-3R, IL5R, IL-6R, IL-12R, GM-CSFR, oncostatin M receptor (OSMR), VEGF receptor, FGF receptor, hPDGF receptor, T cell receptor, MHC proteins, microglobulin-$\beta$, CTLA4, B7 molecule, neuregulin, coagulation factor XIII, NF-$\kappa$B, IL6-IL6R, beta-galactosidase and superoxide dismutase or an isoform, mutein, fused protein, or fragment thereof comprising at least one Ig-like domain.

11. The method according to claim 10, wherein the protein is IL-18BP.

12. The method according to claim 1, wherein the purification factor of the eluted protein is in the range of 11 and 94 fold.

13. The method according to claim 12, wherein the purification factor of the eluted protein is 94 fold.

14. The method according to claim 1, wherein the concentration factor of the eluted protein is in the range of 1.5 and 3.1 fold.

15. The method according to claim 14, wherein the concentration factor of the eluted protein is 3.1 fold.

16. The method according to claim 1, wherein the yield of the eluted protein is in the range of 73 and 98%.

17. The method according to claim 16, wherein the yield of the eluted protein is about 85%.

18. The method according to claim 1, wherein the purification factor of the eluted protein is in about 94 fold.

* * * * *